United States Patent [19]
Chatterjee et al.

[11] Patent Number: 6,083,944
[45] Date of Patent: Jul. 4, 2000

[54] QUINOLINE-CONTAINING α-KETOAMIDE CYSTEINE AND SERINE PROTEASE INHIBITORS

[75] Inventors: Sankar Chatterjee, Wynnewood; John P. Mallamo, Glenmoore; Derek Douglas Dunn, Thorndale, all of Pa.; Kurt Allen Josef, Wilmington, Del.; Zi-Qiang Gu, Reston, Va.; Robert A. Daines, Lansdale, Pa.; William Dennis Kingsbury, Phoenixville, Pa.; Israel Pendrak, Ambler, Pa.; Kelvin C. Sham, King of Prussia, Pa.

[73] Assignees: Cephalon, Inc., West Chester; Smithkline Beecham Corp., Philadelphia, both of Pa.

[21] Appl. No.: 09/167,193

[22] Filed: Oct. 6, 1998

Related U.S. Application Data

[60] Provisional application No. 60/061,267, Oct. 7, 1997.
[51] Int. Cl.[7] .................. A61K 31/47; A61K 31/445; C07D 215/12; C07D 215/14; C07D 215/20
[52] U.S. Cl. .................. 514/235.2; 514/311; 514/312; 544/128; 546/153; 546/156; 546/169
[58] Field of Search .................. 546/153, 156, 546/169; 514/311, 312, 235.2; 544/128

[56] References Cited

U.S. PATENT DOCUMENTS

| | | | |
|---|---|---|---|
| 5,034,376 | 7/1991 | Hoover et al. | 514/18 |
| 5,162,500 | 11/1992 | Takeuchi et al. | 530/330 |
| 5,340,825 | 8/1994 | Horwell et al. | 514/339 |
| 5,444,042 | 8/1995 | Bartus et al. | 514/2 |
| 5,514,694 | 5/1996 | Powers et al. | 514/357 |
| 5,563,127 | 10/1996 | Amparo et al. | 514/64 |
| 5,610,297 | 3/1997 | Powers | 544/168 |
| 5,614,649 | 3/1997 | Iqbal et al. | 554/56 |
| 5,646,121 | 7/1997 | Häbich et al. | 514/18 |
| 5,650,508 | 7/1997 | Powers | 544/168 |
| 5,658,885 | 8/1997 | Lee et al. | 514/19 |
| 5,698,538 | 12/1997 | Amparo et al. | 514/64 |

FOREIGN PATENT DOCUMENTS

| | | |
|---|---|---|
| 0 604 183 A1 | 6/1994 | European Pat. Off. . |
| WO 95/00535 | 1/1995 | WIPO . |
| WO 96/14857 | 5/1996 | WIPO . |
| WO 96/20689 | 7/1996 | WIPO . |
| WO 96/39385 | 12/1996 | WIPO . |

OTHER PUBLICATIONS

Amparo, E. C. et al., "Preparation of .alpha.–aminoboronic acid and ester as inhibitors of thrombin", Chemical Abstract, 1996, vol. 125(17), p. 1172, Abstract No. 222432.

Amparo, E.C. et al., "Boronic acid and ester inhibitors of thrombin", Chemical Abstract, 1997, vol. 126(3), p. 594, Abstract No. 31466.

Nagase, H. et al., "Preparation of morphinan derivatives as analgesics and diuretics", Chemical Abstract, 1994, vol. 120(13), p. 1236, Abstract No. 164625.

Tsushima, T. et al., "Preparation of amino acid derivatives as digestive tract hormone antagonists", Chemical Abstract, 1992, vol. 116(25), p. 838, Abstract No. 256040.

Bihovsky et al., "Preparation of benzothiazine–and related heterocyclic group containing amino acids as cysteine and serine protease inhibitors", Chemical Abstract, 1998, vol. 129, WO 98/21186, Abstract No. 28214.

Giardina, G.A.M. et al., Discovery of a Novel Class of Selective Non–Peptide Antagonists for the Human Neurokinin–3 Receptor. 1. Indentification of the 4–Quinolinecarboxamide Framework, *J. Med. Chem.*, 1997, 40, 1794–1807.

Harbeson, S.L. et al., "Stereospecific Synthesis of Peptidyl β–Keto Amides as Inhibitors of Calpain", *J. Med. Chem.*, 1994, 37, 2918–2929.

Lehninger, *Biochemistry*, Second Edition, Worth Publishers, Inc., 1975, 73–75.

Meyer, S.L. et al., "Biologically active monomeric and heterodimeric recombinant human calpain I produced using the baculovirus expression system", *Biochem. J.*, 1996, 314, 511–519.

*Primary Examiner*—Mukund J. Shah
*Assistant Examiner*—Deepak R. Rao
*Attorney, Agent, or Firm*—Woodcock Washburn Kurtz Mackiewicz & Norris LLP

[57] ABSTRACT

The present invention is directed to quinoline-containing α-ketoamide inhibitors of cysteine and serine proteases are disclosed. Methods for making these compounds, and methods for using the same are also disclosed.

21 Claims, No Drawings

QUINOLINE-CONTAINING α-KETOAMIDE CYSTEINE AND SERINE PROTEASE INHIBITORS

CROSS REFERENCE TO RELATED APPLICATIONS

This application claims benefit of U.S. Provisional Application Ser. No. 60/061,267, filed Oct. 7, 1997, the disclosure of which is hereby incorporated herein by reference in its entirety.

FIELD OF THE INVENTION

This invention relates to quinoline-containing α-ketoamide inhibitors of cysteine and serine proteases, methods for making these compounds, and methods for using the same.

BACKGROUND OF THE INVENTION

Numerous cysteine and serine proteases have been identified in human tissues. A "protease" is an enzyme which degrades proteins into smaller components (peptides). The terms "cysteine protease" and "serine protease" refer to proteases which are distinguished by the presence therein of a cysteine or serine residue which plays a critical role in the catalytic process. Mammalian systems, including humans, normally degrade and process proteins via a variety of enzymes including cysteine and serine proteases. However, when present at elevated levels or when abnormally activated, cysteine and serine proteases may be involved in pathophysiological processes.

For example, calcium-activated neutral proteases ("calpains") comprise a family of intracellular cysteine proteases which are ubiquitously expressed in mammalian tissues. Two major calpains have been identified; calpain I and calpain II. While calpain II is the predominant form in many tissues, calpain I is thought to be the predominant form in pathological conditions of nerve tissues. The calpain family of cysteine proteases has been implicated in many diseases and disorders, including neurodegeneration, stroke, Alzheimer's, amyotrophy, motor neuron damage, acute central nervous system injury, muscular dystrophy, bone resorption, platelet aggregation, cataracts and inflammation. Calpain I has been implicated in excitatory amino-acid induced neurotoxicity disorders including ischemia, hypoglycemia, Huntington's Disease, and epilepsy.

The lysosomal cysteine protease cathepsin B has been implicated in the following disorders: arthritis, inflammation, myocardial infarction, tumor metastasis, and muscular dystrophy. Other lysosomal cysteine proteases include cathepsins C, H, L and S. Interleukin-1β converting enzyme ("ICE") is a cysteine protease which catalyzes the formation of interleukin-1β. Interleukin-1β is an immunoregulatory protein implicated in the following disorders: inflammation, diabetes, septic shock, rheumatoid arthritis, and Alzheimer's disease. ICE has also been linked to apoptotic cell death of neurons, which is implicated in a variety of neurodegenerative disorders including Parkinson's disease, ischemia, and amyotrophic lateral sclerosis (ALS).

Cysteine proteases are also produced by various pathogens. The cysteine protease clostripain is produced by *Clostridium histolyticum*. Other proteases are produced by *Trypanosoma cruzi*, malaria parasites *Plasmodium falciparum* and *P. vinckei* and Streptococcus. Hepatitis A viral protease HAV C3 is a cysteine protease essential for processing of picornavirus structural proteins and enzymes.

Exemplary serine proteases implicated in degenerative disorders include thrombin, human leukocyte elastase, pancreatic elastase, chymase and cathepsin G. Specifically, thrombin is produced in the blood coagulation cascade, cleaves fibrinogen to form fibrin and activates Factor VIII; thrombin is implicated in thrombophlebitis, thrombosis and asthma. Human leukocyte elastase is implicated in tissue degenerative disorders such as rheumatoid arthritis, osteoarthritis, atherosclerosis, bronchitis, cystic fibrosis, and emphysema. Pancreatic elastase is implicated in pancreatitis. Chymase, an enzyme important in angiotensin synthesis, is implicated in hypertension, myocardial infarction, and coronary heart disease. Cathepsin G is implicated in abnormal connective tissue degradation, particularly in the lung.

Given the link between cysteine and serine proteases and various debilitating disorders, compounds which inhibit these proteases would be useful and would provide an advance in both research and clinical medicine. The present invention is directed to these, as well as other, important ends.

SUMMARY OF THE INVENTION

The present invention is directed to selected quinoline-containing α-ketoamide inhibitors of cysteine and serine proteases represented by the general Formula I:

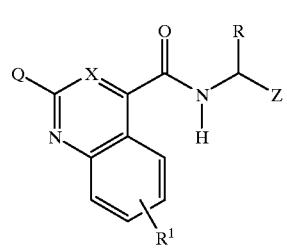

wherein:

X is CH, N, or $CQ^1$, with the proviso that when X is $CQ^1$, at least one of Q or $Q^1$ is H;

R is selected from the group consisting of H, alkyl having from one to about 6 carbons, arylalkyl having from about 7 to about 15 carbons, heteroalkyl in which the ring contains from about 5 to about 14 ring atoms, heteroarylalkyl in which the heteroaryl ring contains from about 5 to about 14 ring atoms, alkoxyalkyl, a side chain of a naturally occurring amino acid in the R or S configuration, and $(CH_2)_n$NH—L, said alkyl, arylalkyl, heteroalkyl, and heteroarylalkyl groups being optionally substituted with one or more J groups;

L is selected from the group consisting of alkoxycarbonyl having from 2 to about 7 carbons, arylalkoxycarbonyl in which the arylalkoxy group contains about 7 to about 15 carbons, $S(=O)_2R^2$, and N-nitroimino;

$R^2$ is selected from the group consisting of lower alkyl, and aryl having from about 6 to about 14 carbons;

$R^1$ is selected from the group consisting of H, halogen, cyano, nitro, sulfonic acid, hydroxyl, alkyl, alkoxy, hydroxymethyl, alkoxymethyl, arylalkyl, carboxyl, alkoxycarbonyl, alkylcarbonyloxy, haloalkyl, $N(RR^3)$, and acyl;

$R^3$ is the same as R;

Q is selected from the group consisting of H, lower alkyl, cycloalkyl, hydroxyl, alkoxy, halogen, arylalkyl having from about 7 to about 15 carbons, arylalkenyl having from about 8 to about 16 carbons, arylalkynyl having from about 8 to about 16 carbons, aryl having from about 6 to about 14 carbons, heteroaryl having from about 5 to about 14 ring atoms, heteroalkyl having from about 5 to about 14 ring atoms, cycloalkyl having from about 3 to about 10 carbons, S—R, S(=O)R, S(=O)$_2$R, N(RR$^3$), and NHS(=O)$_2$R, said arylalkyl, arylalkenyl, arylalkynyl, aryl, heteroaryl, and heteroalkyl groups being optionally substituted with one or more J groups;

$Q^1$ is the same as Q;

Z is COCONH—R$^7$;

R$^7$ is selected from the group consisting of K, —A—N(R$^8$)—G, —O—A—N(R$^8$)—G, —A—SO$_2$N(R$^8$)(R$^9$), and —O—A—SO$_2$N(R$^8$)(R$^9$);

K is selected from the group consisting of alkyl, alkenyl, alkynyl, cycloalkyl, heteroalkyl, heteroaryl, aryl, arylalkyl, heterocycloalkyl, alkoxy, alkoxyalkyl, arylalkyloxy, and N(RR$^3$), said K groups being optionally substituted with one or more J groups;

A is lower alkylene optionally substituted with one or more J groups;

R$^8$ is selected from the group consisting of H and lower alkyl;

R$^9$ is selected from the group consisting of H, alkyl, aryl, and heterocyclyl, said alkyl, aryl, and heterocyclyl groups being optionally substituted with one or more J groups;

G is selected from the group consisting of C(=O)aryl, C(=O)heteroaryl, C(=O)heteroalkyl, alkanoyl, C(=S)NH(aryl), C(=O)NH(aryl), C(=O)NH(cycloalkyl), CO$_2$(aryl), C(=O)alkyl, CO$_2$(alkyl), CO$_2$(arylalkyl), alkylsulfonyl, alkenylsulfonyl, arylsulfonyl, heteroarylsulfonyl, a side chain of a naturally occurring amino acid in the R or S configuration, a blocking group, and SO$_2$N(RR$^3$), said G groups being optionally substituted with one or more J groups;

J is selected from the group consisting of H, halogen, cyano, nitro, hydroxyl, alkyl, alkoxy, aryl, arylalkyl, alkoxycarbonyl, alkylcarbonyloxy, alkenylcarbonyloxy, haloalkyl, aminoalkyl, haloalkoxy, SO$_2$N(RR$^3$), SO$_2$NH(aryl), SO$_2$NH(heteroaryl), NHC(=O)NH(aryl), NH(C=O)NH(heteroaryl), NHSO$_2$(aryl), NHC(=O)alkyl, NHC(=O)aryl, NHC(=O)heteroaryl, N(RR$^3$), and NH=C(NH$_2$)$_2$;

n is an integer from 2 to 6;

or a pharmaceutically acceptable salt thereof;

with the proviso that when R$^7$ is K, then Q is selected from the group consisting of optionally substituted arylalkenyl and optionally substituted arylalkynyl; and with the further proviso that when K is alkyl, then X is not CH when Q is optionally substituted arylalkynyl.

In some preferred embodiments of the compounds of Formula I, X is CH. In further preferred embodiments of the compounds of Formula I, R is selected from the group consisting of alkyl having from 2 to 4 carbons, and arylalkyl, with benzyl being particularly preferred.

In some preferred embodiments of the compounds of Formula I, R$^1$ is H or alkoxy, with H being preferred.

In some preferred embodiments of the compounds of Formula I, Q is selected from the group consisting of arylalkynyl, aryl and halo, with phenylalkynyl being preferred.

In further preferred embodiments of the compounds of Formula I, A is selected from the group consisting of (CH$_2$)$_n$ wherein n is 2 or 3, and (CH$_2$)$_v$CH$_2$—J where v is an integer from 1 to 6. When A is (CH$_2$)$_v$CH$_2$—J, v is preferably 2 or 3.

In some preferred embodiments of the compounds of Formula I, K is selected from the group consisting of alkyl, hydroxyalkyl, haloalkyl, alkynyl, heterocycloalkyl, arylalkyl, and heteroalkyl.

In further preferred embodiments of the compounds of Formula I, G is selected from the group consisting of substituted or unsubstituted C(=)aryl, C(=)heteroaryl, arylsulfonyl, and heteroarylsulfonyl. Preferably, G is selected from the group consisting of unsubstituted arylsulfonyl, substituted arylsulfonyl, unsubstituted heteroarylsulfonyl and substituted heteroarylsulfonyl.

In some preferred embodiments of the compounds of Formula I, X is CH, Z is COCONH—K, R$_1$ is H, and R is selected from the group consisting of alkyl having from 2 to 4 carbons and arylalkyl, with benzyl being preferred.

In some especially preferred embodiments of the compounds of the Formula I, X is CH, Z is COCONH—K, R$_1$ is H, R is selected from the group consisting of alkyl having from 2 to 4 carbons and arylalkyl, with benzyl being preferred, and Q is arylalkynyl, with phenylethynyl being preferred.

In some especially preferred embodiments of the compounds of Formula I, Q, X, R$^1$, R, and Z are selected from the group of substituents listed in Tables 2 to 5, infra. Particularly preferred embodiments of the compounds of Formula I are listed in Tables 2 to 5, infra.

Because the quinoline-containing α-ketoamides of the invention inhibit cysteine proteases and serine proteases, they can be used in both research and therapeutic settings.

In a research environment, preferred compounds having defined attributes can be used to screen for natural and synthetic compounds which evidence similar characteristics in inhibiting protease activity. The compounds can also be used in the refinement of in vitro and in vivo models for determining the effects of inhibition of particular proteases on particular cell types or biological conditions.

In a therapeutic setting, given the connection between cysteine proteases and certain defined disorders, and serine proteases and certain defined disorders, compounds of the invention can be utilized to alleviate, mediate, reduce and/or prevent disorders which are associated with abnormal and/or aberrant activity of cysteine proteases and/or serine proteases.

In preferred embodiments, compositions are provided for inhibiting a serine protease or a cysteine protease comprising a compound of the invention. In other preferred embodiments, methods are provided for inhibiting serine proteases or cysteine proteases comprising contacting a protease selected from the group consisting of serine proteases and cysteine proteases with an inhibitory amount of a compound of the invention.

Methodologies for making the present quinoline-containing α-ketoamide inhibitors are also disclosed. Other useful methodologies will be apparent to those skilled in the art, once armed with the present disclosure. These and other features of the compounds of the subject invention are set forth in more detail below.

DETAILED DESCRIPTION

Disclosed herein are selected quinoline-containing α-ketoamide serine and cysteine protease inhibitors, which are represented by the following Formula I:

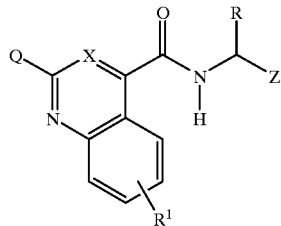

wherein:

X is CH, N, or CQ¹, with the proviso that when X is CQ¹, at least one of Q or Q¹ is H;

R is selected from the group consisting of H, alkyl having from one to about 6 carbons, arylalkyl having from about 7 to about 15 carbons, heteroalkyl in which the ring contains from about 5 to about 14 ring atoms, heteroarylalkyl in which the heteroaryl ring contains from about 5 to about 14 ring atoms, alkoxyalkyl, a side chain of a naturally occurring amino acid in the R or S configuration, and $(CH_2)_n$NH-L, said alkyl, arylalkyl, heteroalkyl, and heteroarylalkyl groups being optionally substituted with one or more J groups;

L is selected from the group consisting of alkoxycarbonyl having from 2 to about 7 carbons, arylalkoxycarbonyl in which the arylalkoxy group contains about 7 to about 15 carbons, $S(=O)_2R^2$, and N-nitroimino;

$R^2$ is selected from the group consisting of lower alkyl, and aryl having from about 6 to about 14 carbons;

$R^1$ is selected from the group consisting of H, halogen, cyano, nitro, sulfonic acid, hydroxyl, alkyl, alkoxy, hydroxymethyl, alkoxymethyl, arylalkyl, carboxyl, alkoxycarbonyl, alkylcarbonyloxy, haloalkyl, $N(RR^3)$, and acyl;

$R^3$ is the same as R;

Q is selected from the group consisting of H, lower alkyl, cycloalkyl, hydroxyl, alkoxy, halogen, arylalkyl having from about 7 to about 15 carbons, arylalkenyl having from about 8 to about 16 carbons, arylalkynyl having from about 8 to about 16 carbons, aryl having from about 6 to about 14 carbons, heteroaryl having from about 5 to about 14 ring atoms, heteroalkyl having from about 5 to about 14 ring atoms, cycloalkyl having from about 3 to about 10 carbons, S—R, $S(=O)R$, $S(=O)_2R$, $N(RR^3)$, and $NHS(=O)_2R$, said arylalkyl, arylalkenyl, arylalkynyl, aryl, heteroaryl, and heteroalkyl groups being optionally substituted with one or more J groups;

$Q^1$ is the same as Q;

Z is COCONH—$R^7$;

$R^7$ is selected from the group consisting of K, —A—N($R^8$)—G, —O—A—N($R^8$)—G, A—$SO_2N(R^8)(R^9)$, and —O—A—$SO_2N(R^8)(R^9)$;

K is selected from the group consisting of alkyl, alkenyl, alkynyl, cycloalkyl, heteroalkyl, heteroaryl, aryl, arylalkyl, heterocycloalkyl, alkoxy, alkoxyalkyl, arylalkyloxy, and $N(RR^3)$, said K groups being optionally substituted with one or more J groups;

A is lower alkylene optionally substituted with one or more J groups;

$R^8$ is selected from the group consisting of H and lower alkyl;

$R^9$ is selected from the group consisting of H, alkyl, aryl, and heterocyclyl, said alkyl, aryl, and heterocyclyl groups being optionally substituted with one or more J groups;

G is selected from the group consisting of C(=O)aryl, C(=O)heteroaryl, C(=O)heteroalkyl, alkanoyl, C(=S)NH(aryl), C(=O)NH(aryl), C(=O)NH(cycloalkyl), $CO_2$(aryl), C(=O)alkyl, $CO_2$(alkyl), $CO_2$(arylalkyl), alkylsulfonyl, alkenylsulfonyl, arylsulfonyl, heteroarylsulfonyl, a side chain of a naturally occurring amino acid in the R or S configuration, a blocking group, and $SO_2N(RR^3)$, said G groups being optionally substituted with one or more J groups;

J is selected from the group consisting of H, halogen, cyano, nitro, hydroxyl, alkyl, alkoxy, aryl, arylalkyl, alkoxycarbonyl, alkylcarbonyloxy, alkenylcarbonyloxy, haloalkoxy, aminoalkyl, haloalkoxy, $SO_2N(RR^3)$, $SO_2NH$(aryl) $SO_2NH$(heteroaryl), NHC(=O)NH(aryl), NH(C=O)NH(heteroaryl), $NHSO_2$(aryl), NHC(=O)alkyl, NHC(=O)aryl, NHC(=O)heteroaryl, $N(RR^3)$, and NH=C($NH_2$)$_2$;

n is an integer from 2 to 6;

or a pharmaceutically acceptable salt thereof;

with the proviso that when $R^7$ is K, then Q is selected from the group consisting of optionally substituted arylalkenyl and optionally substituted arylalkynyl; and with the further proviso that when K is alkyl, then X is not CH when Q is optionally substituted arylalkynyl.

It is recognized that various stereoisomeric forms of the compounds of Formula I may exist. Preferred compounds of the invention have the L-configuration at the carbon to which the substituent R is attached. However, reacemates and individual enantiomers and mixtures thereof form part of the present invention.

As used herein, the term "quinoline" denotes a "quinoline" or a "quinoline N-oxide" structure.

In the compounds of Formula I, where a bond to a substituent is shown to cross the bond connecting two atoms in a ring, it is intended that such substituent may be bound to any atom in the ring.

As used herein, the term "alkyl" includes straight-chain, branched and cyclic hydrocarbon groups such as, for example, methyl, ethyl, propyl, isopropyl, butyl, isobutyl, sec-butyl, tert-butyl, pentyl, 1-ethylpentyl, hexyl, octyl, cyclopropyl, methylcyclopentyl, cyclohexyl, and adamantane groups. Preferred alkyl groups have 1 to about 10 carbon atoms, with 1 to about 6 carbon atoms (i.e., "lower alkyl") being preferred. "Lower alkylene" groups are branched or unbranched alkylene groups of 1 to about 6 carbon atoms such as, for example, ethylene (—$CH_2CH_2$—), propylene, butylene, hexylene, 1-methylethylene, 2-methylethylene, and 2-methylpropylene. "Acyl" (i.e., "alkanoyl") groups are alkylcarbonyl groups. "Aryl" groups are aromatic cyclic compounds including but not limited to phenyl, tolyl, naphthyl, anthracyl, phenanthryl, pyrenyl, biphenyl, and xylyl. Preferred aryl groups include phenyl and naphthyl. The term "carbocyclic", as used herein, refers to cyclic groups in which the ring portion is composed solely of carbon atoms. The term "halogen" refers to F, Cl, Br, and I atoms. The term "arylalkyl" (or "aralkyl") denotes alkyl groups which bear aryl groups, for example, benzyl groups.

As used herein, "alkoxy" groups are alkyl groups linked through an oxygen atom. Examples of alkoxy groups include methoxy (—$OCH_3$) and ethoxy (—$OCH_2CH_3$) groups. In general, the term "oxy" when used as a suffix denotes attachment through an oxygen atom. Thus, alkoxycarbonyl groups are carbonyl groups which contain an alkoxy substituent, i.e., groups of general formula —C(=O)—O—R, where R is alkyl. The term "alkoxyalkyl" denotes an alkoxy group attached to an aklyl group. The term "aryloxy" denotes an aryl group linked through an oxygen atom, and the term "arylalkyloxy" denotes an arylalkyl group linked through an oxygen atom.

As used herein, the term "alkenyl" is intended to include straight-chain or branched hydrocarbon chains having at least one carbon—carbon double bond. Examples of alkenyl groups include ethenyl and propenyl groups. Arylalkenyl groups are alkenyl groups that have one or more aryl groups appended thereto. As used herein, the term "alkynyl" is intended to include straight-chain or branched hydrocarbon chains having at least one carbon—carbon triple bond. Examples of alkynyl groups include ethynyl and propynyl groups. Arylalkynyl groups are alkynyl groups that have one or more aryl groups appended thereto.

The terms "heterocycle", "heterocyclyl", and "heterocyclic" refer to cyclic groups in which a ring portion includes at least one heteroatom such as O, N or S. Heterocyclic groups include "heteroaryl" as well as "heteroalkyl" groups. Preferred "heteroaryl" groups include pyridyl, pyrimidyl, pyrrolyl, furyl, thienyl, imidazolyl, triazolyl, tetrazolyl, quinolyl, isoquinolyl, benzimidazolyl, thiazolyl, bipyridyl, phthalimido, and benzothiazolyl. The term "heterocycloalkyl" denotes a heterocycle attached through a lower alkyl group. The term "heteroaryl" denotes aryl groups having one or more hetero atoms contained within an aromatic ring. The term "heteroarylalkyl" denotes a heteroaryl group attached through an alkyl group. The term "heteroalkyl" denotes a heterocyclic group which contains at least one saturated carbon atom in the heterocyclic ring. Examples of heteroalkyl groups include piperidine, dihydropyridine, tetrahydroisoquinyl, and ε-caprolactam groups.

As used herein, the term "amino acid" denotes a molecule containing both an amino group and a carboxyl group. As used herein the term "L-amino acid" denotes an α-amino acid having the L-configuration around the α-carbon, that is, a carboxylic acid of general formula CH(COOH)(NH$_2$)-(side chain), having the L-configuration. The term "D-amino acid" similarly denotes a carboxylic acid of general formula CH(COOH)(NH$_2$)-(side chain), having the D-configuration around the α-carbon. Side chains of L-amino acids include naturally occurring and non-naturally occurring moieties. Nonnaturally occurring (i.e., unnatural) amino acid side chains are moieties that are used in place of naturally occurring amino acid sidechains in, for example, amino acid analogs. See, for example, Lehninger, *Biochemistry*, Second Edition, Worth Publishers, Inc, 1975, pages 73–75. One representative amino acid side chain is the lysyl side chain, —(CH$_2$)$_4$—NH$_2$. Other representative α-amino acid side chains are shown below in Table 1.

TABLE 1

| | |
|---|---|
| CH$_3$— | HS—CH$_2$— |
| HO—CH$_2$— | HO$_2$C—CH(NH$_2$)—CH$_2$—S—S—CH$_2$— |
| C$_6$H$_5$—CH$_2$— | CH$_3$—CH$_2$— |
| HO—C$_6$H$_4$—CH$_2$— | CH$_3$—S—CH$_2$—CH$_2$— |
| | CH$_3$—CH$_2$—S—CH$_2$—CH$_2$— |
| | HO—CH$_2$—CH$_2$— |
| 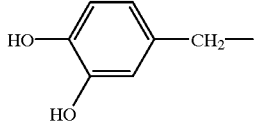 | CH$_3$—CH(OH)— |
| | HO$_2$C—CH$_2$—NHC(=O)—CH$_2$— |
| 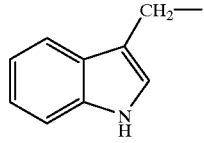 | 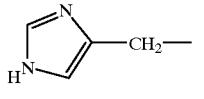 |
| | HO$_2$C—CH$_2$—CH$_2$— |
| 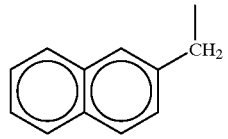 | NH$_2$C(=O)—CH$_2$—CH$_2$— |
| | (CH$_3$)$_2$—CH— |
| | (CH$_3$)$_2$—CH—CH$_2$— |
| | CH$_3$—CH$_2$—CH$_2$— |
| | H$_2$N—CH$_2$—CH$_2$CH$_2$— |
| 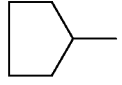 | H$_2$N—C(=NH)—NH—CH$_2$—CH$_2$—CH$_2$— |
| | H$_2$N—C(=O)—NH—CH$_2$—CH$_2$—CH$_2$— |
| | CH$_3$—CH$_2$—CH(CH$_3$)— |
| | CH$_3$—CH$_2$—CH$_2$—CH$_2$— |
| | H$_2$N—CH$_2$—CH$_2$—CH$_2$—CH$_2$— |
| 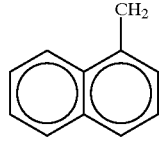 | |

Functional groups present in the compounds of Formula I may contain blocking groups. Blocking groups are known per se as chemical functional groups that can be selectively appended to functionalities, such as hydroxyl groups, amino groups, thio groups, and carboxyl groups. Protecting groups are blocking groups which can be readily removed from functionalities. These groups are present in a chemical compound to render such functionality inert to chemical reaction conditions to which the compound is exposed. Any of a variety of protecting groups may be employed with the present invention. Examples of such protecting groups are the benzyloxycarbonyl (Cbz; Z), toluenesulfonyl, t-butoxycarbonyl, methyl ester, and benzyl ether groups. Other preferred protecting groups according to the invention may be found in Greene, T. W. and Wuts, P. G. M., *"Protective Groups in Organic Synthesis"* 2d. Ed., Wiley & Sons, 1991.

Further blocking groups useful in the compounds of the present invention include those that bear acyl, aroyl, alkyl, alkanesulfonyl, arylalkanesulfonyl, or arylsulfonyl substituents on their amino group. Other useful blocking groups include aklyl ethers, e.g., the methyl ether of serine.

The disclosed compounds of the invention are useful for the inhibition of cysteine proteases and serine proteases. As used herein, the terms "inhibit" and "inhibition" mean having an adverse effect on enzymatic activity. An inhibitory amount is an amount of a compound of the invention effective to inhibit a cysteine and/or serine protease.

Pharmaceutically acceptable salts of the cysteine and serine protease inhibitors also fall within the scope of the compounds as disclosed herein. The term "pharmaceutically acceptable salts" as used herein means an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable organic amine addition salts are salts with morpholine and piperdine. Examples of pharmaceutically acceptable amino acid addition salts are salts with lysine, glycine, and phenylalanine.

Compounds provided herein can be formulated into pharmaceutical compositions by admixture with pharmaceutically acceptable excipients and carriers. As noted above, such compositions may be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, transdermal patches; or prepared in other suitable fashions for these and other forms of administration as will be apparent to those skilled in the art.

The composition may conveniently be administered in unit dosage form and may be prepared by any of the methods well known in the pharmaceutical art, for example, as described in *Remington's Pharmaceutical Sciences* (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, cyclodextrins and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for transdermal patches are preferably lipophilic emulsions.

The materials for this invention can be employed as the sole active agent in a pharmaceutical or can be used in combination with other active ingredients which could facilitate inhibition of cysteine and serine proteases in diseases or disorders.

The concentrations of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention may be provided in effective inhibitory amounts in an aqueous physiological buffer solution containing about 0.1 to 10% w/v compound for parenteral administration. Typical dose ranges are from about 1 $\mu$g/kg to about 1 g/kg of body weight per day; a preferred dose range is from about 0.01 mg/kg to 100 mg/kg of body weight per day. Such formulations typically provide inhibitory amounts of the compound of the invention. The preferred dosage of drug to be administered is likely, however, to depend on such variables as the type or extent of progression of the disease or disorder, the overall health status of the particular patient, the relative biological efficacy of the compound selected, and formulation of the compound excipient, and its route of administration.

As used herein, the term "contacting" means directly or indirectly causing at least two moieties to come into physical association with each other. Contacting thus includes physical acts such as placing the moieties together in a container, or administering moieties to a patient. Thus, for example administering a compound of the invention to a human patient evidencing a disease or disorder associated with abnormal and/or aberrant activity of such proteases falls within the scope of the definition of the term "contacting".

The invention is further illustrated by way of the following examples which are intended to elucidate the invention. These examples are not intended, nor are they to be construed, as limiting the scope of the disclosure.

EXAMPLES

Examples 1–158

The compounds shown in Tables 2 through 5 were prepared using conditions described in the "General Methods" section below. Enzyme inhibitory activity ($IC_{50}$) was determined as described in Examples 159 and 160.

In all Examples, $R^1$ is H unless otherwise noted.

General Methods

Thin layer chromatography was performed using silica gel coated plates (MK6F 60A, size 1×3 in, layer thickness 250 $\mu$m, Whatman Inc.). Preparative thin layer chromatography was performed using silica gel coated plates (size 20×20 in, layer thickness 1000 micron, Analtech). Preparative column chromatography was carried out using Merck silica gel, 40–63 $\mu$m, 230–400 mesh. $^1$H NMR spectra were recorded on a GE QE300 Plus spectrometer at 300 MHZ using tetramethylsilane as internal standard. Electrospray mass spectra were recorded on a VG platform II instrument (Fisons Instruments).

Compounds were prepared following one of the general methods A, B, C or D.

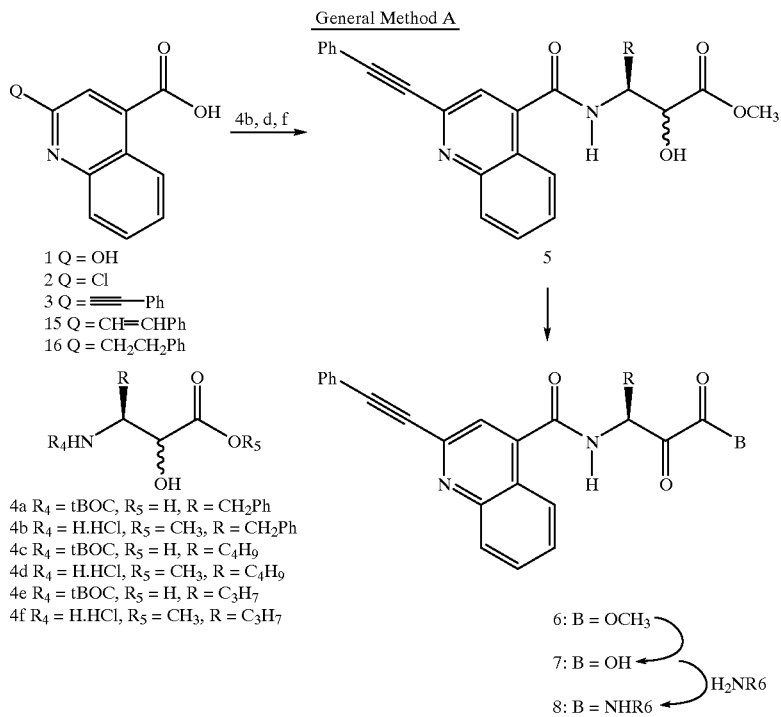

Preparation of Compound 2

A mixture of compound of formula 1 (20 g, 0.106 mol) and phosphorous oxychloride (50 mL, 0.54 mol) was held at reflux for 3 hours. After cooling, the reaction mixture was slowly poured into ice-water and a white precipitate was formed. The precipitate was filtered, thoroughly washed with cold water, and redissolved in ethyl acetate (300 mL). The solution was dried over anhydrous sodium sulfate. Filtration and solvent removal gave 14.78 g of compound 2 which was used without further purification.

Compound 2: tan solid; $^1$H-NMR (DMSO-d$_6$) δ8.60 (d, 1H), 8.00 (d, 1H), 7.90 (s, 1H), 7.80 (t, 1H), 7.70 (t, 1H). MS m/e 208 and 210 (M+H with isotopes of chlorine).

Preparation of Compound 3

A mixture of compound 2 (20 g, 0.0966 mol), phenylacetylene (13.02 g, 14 mL, 0.127 mol), (PPh$_3$)PdCl$_2$ (1.40 g, 0.00193 mol), CuI (0.42 g, 0.00386 mol), triethylamine (19.66 g, 27 mL, 0.192 mol) and anhydrous DMSO (150 mL) was heated at 60–70° C. for 3 hours. After cooling, the reaction mixture was slowly poured into ice-water (300 mL). The aqueous solution was acidified with 2 N HCl and extracted into methylene chloride (3×700 mL). The organic layer was washed with brine (3×250 mL), dried (anhydrous sodium sulfate) and concentrated to give a residue which, on recrystallization from methylene chloride-hexanes, yielded 23.8 g of compound 3.

Compound 3: white solid; $^1$H-NMR (DMSO-d$_6$) δ8.60 (d, 1H), 8.10 (d, 1H), 8.05 (s, 1H), 7.85 (t, 1H), 7.70 (m, 3H), 7.45 (m, 3H). MS m/e 274 (M+H).

Preparation of Compound 4a

Compound 4a, and related hydroxy-acids used in this study, were synthesized following a general procedure of Harbeson et al., *J. Med. Chem.* 1994, 37, 2918–2929.

Preparation of Compound 4b

To a cooled (−10° C.) solution of compound 4a (4.30 g, 0.015 mol) in anhydrous methanol (50 mL) was added slowly thionyl chloride (3.20 mL). After 0.5 hour, the cooling bath was removed, the mixture was stirred for an additional 16 hours and concentrated to give a residue. Trituration with ethyl acetate (30 mL) gave a white solid. The solid was separated by filtration and dried to give 3.50 g of compound 4b which was used directly in the next step; MS m/e 210 (M+H).

Preparation of Compound 5 (R=Benzyl)

To a cooled (0° C.) solution of compound 3 (0.88 g, 0.0032 mol) in anhydrous DMF (10 mL) was added N-methylmorpholine (0.98 g, 0.0096 mol) followed by 1-HOBt (0.43 g, 0.0032 mol) and BOP (1.70 g, 0.0039 mol). The mixture was stirred for 15 minutes and to it was added compound 4b (0.95 g, 0.0039 mol). The cooling bath was removed and the mixture was stirred for 4 hours, poured into ice-water (40 mL) and extracted into ethyl acetate (3×40 mL). The organic layer was washed with 2% citric acid solution (2×40 mL), 2% sodium bicarbonate solution (2×40 mL), brine (1×50 mL) and dried over anhydrous sodium sulfate. Solvent evaporation under reduced pressure gave a crude material which was purified by flash column chromatography (eluant: 40% ethyl acetate in hexanes) to produce 1.10 g of compound 5.

Compound 5 (Diastereomeric mixture): white solid; $^1$H-NMR (CDCl$_3$) δ8.10 (d, 1H), 7.80–7.20 (2 sets of m, 14H), 6.40 (2 sets of d, 1H), 5.00 (m,1H), 4.60 and 4.30 (2 sets of t, 1H), 3.85 and 3.75 (2 singlets, 3H), 3.50 and 3.35 (2 sets of d, 1H), 3.10 and 3.00 (2 sets of dd, 2H). MS m/e 465(M+H).

Preparation of Compound 6 (R=Benzyl)

To a cooled (0° C.) solution of compound 5 (4.33 g, 9.33 mmol) in 1:1 anhydrous methylene chloride and anhydrous acetonitrile (60 mL) was slowly added Dess-Martin periodinane reagent (7.90 g, 18.66 mmol). The cooling bath was removed and the mixture was stirred for an additional 2 hours. The mixture was then diluted with methylene chloride (50 mL) and washed with 10% sodium thiosulfate solution (5×50 mL), saturated sodium bicarbonate solution (2×50 mL), and brine (1×50 mL). Drying (anhydrous sodium sulfate) and solvent removal under reduced pressure gave a residue which was purified by flash column chromatography (eluant: 1:1 EtOAc-hexanes) to yield 3.3 g of compound 6.

Compound 6: white solid; $^1$H-NMR (CDCl$_3$) δ8.20–7.20 (m, 15H), 6.65 (d, 1H), 5.80 (q, 1H), 3.95 (s, 3H), 3.50 (dd, 1H), 3.20 (dd, 1H). MS m/e 463(M+H).

Preparation of Compound 7 (R=Benzyl)

A mixture of compound 6, (1.20 g, 2.60 mmol), 1 N NaOH (6.5 mL) and MeOH (15 mL) was stirred at room temperature for 1.5 hours. TLC (50% EtOAc in methylene chloride) showed the complete disappearence of compound 6. The reaction mixture was concentrated at the rotavapor and redissolved in water (25 mL). The aqueous layer was washed with ether (2×15 mL) and acidified with 1 N HCl. The aqueous layer was then extracted into EtOAc (3×50 mL) and the combined ethyl acetate layer was washed with brine (1×20 mL), dried (MgSO4) and concentrated at the rotavapor to give 1.17 g of compound 7. $^1$H-NMR (CDCl$_3$) of an aliquot showed absence of a COOCH$_3$ peak at δ3.95; MS m/e 449 (M+H).

Preparation of Compound 8

Compound 8 was prepared, for example, by coupling compound 7 with an amine in the presence of NMM/HOBt/BOP/DMF, as described for the synthesis of compound 5. Purification was achieved by passing a solution of the crude material in methylene chloride or ethyl acetate through Sep-Pak® Vac 6cc (1 g) silica cartidge (Waters Corporation, Milford, Mass.) and eluting with methylene chloride followed by mixtures of methylene chloride and ethyl acetate.

Harbeson et al. reported (*J. Med. Chem.* 1994, 37, 2918–2929) that silica gel chromatography (of a ketoamide) epimerizes the chiral center at P$_1$.

General Method B

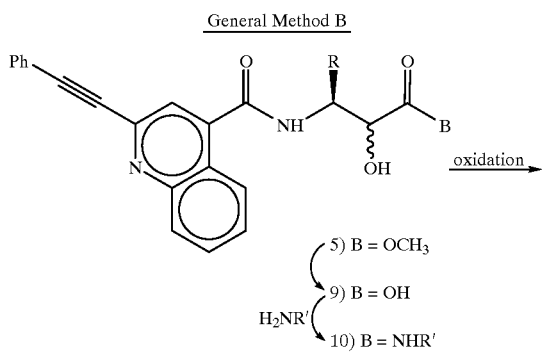

-continued

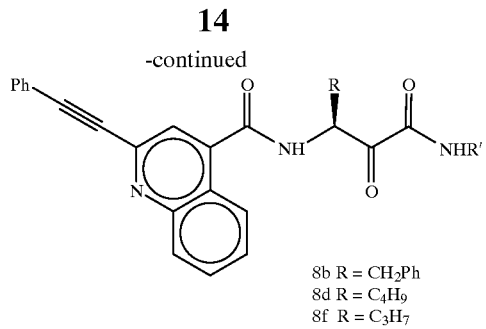

8b R = CH$_2$Ph
8d R = C$_4$H$_9$
8f R = C$_3$H$_7$

In General Method B, compounds of the formula 5 from General Method A were hydrolyzed to compounds of formula 9, following the same procedure as described for the synthesis of compound 7. Compounds of formula 9 were then coupled with an amine (NMM/HOBt/BOP/DMF), as described for the synthesis of compound 5, to produce the α-hydroxyamides (compound 10). Dess-Martin oxidation of compounds of formula 10 generated the ketoamides (compound 8) of the invention, which were used as such or recrystallized from organic solvents.

General Method C

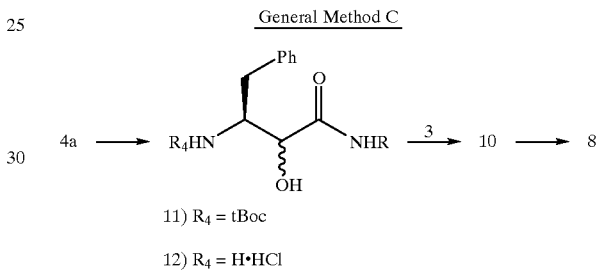

11) R$_4$ = tBoc
12) R$_4$ = H•HCl

In General Method C, compound 4a (General Method A) was initially coupled to an amine (NMM/HOBt/BOP/DMF), as described for the synthesis of compound 5, to generate compound 11, tBoc-deprotection was carried out under standard conditions (4 N HCl in dioxane, room temperature) to generate the amine salt, compound 12. Coupling of compound 12 with compound 3 (NMM/HOBt/BOP/DMF) as described for the synthesis of compound 5 produced compound 10.

Dess-Martin oxidation of compound 10 generated compound 8.

General Method D

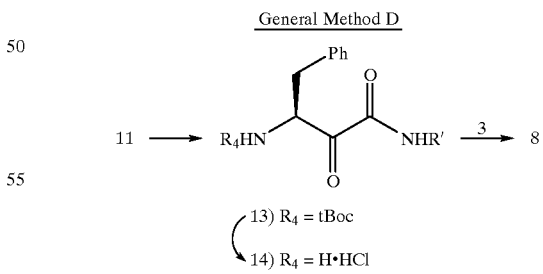

13) R$_4$ = tBoc
14) R$_4$ = H•HCl

In General Method D, compound 11 from General Method C was oxidized to generate compound 13, which on tBoc-deprotection generated compound 14. Coupling of compound 3 with compound 14 produced the ketoamide of the invention (compound 8).

It should be noted that although the General Methods A, B, C and D display only 2-phenylethynylquinoline (3) as the quinoline component of the invention, they are also valid for all other quinoline-4-carboxylic acids shown. Similarly, the methods are also valid for the different hydroxyacids derived from Leu, Nle (4c), Nva (4e), or by extension to any α-hydroxy-β-amino acid, in place of compound 4a (derived from phenylalanine).

Preparation of Intermediates

Preparation of Compounds 15 and 16

Compound 3 (1.00 g, 3.66 mmol) was dissolved in DMF (14 mL), and the solution was stirred and hydrogenated at atmospheric pressure over 10% Pd-C (170 mg) for 50 hours (more 10% Pd-C (230 mg total) was added after 23 and 29 h). After filtration, the solvent was evaporated in vacuo at 40° C. The residue was dissolved in methylene chloride, and the solution was rinsed twice with water and twice with brine, then dried over anhydrous $MgSO_4$. Evaporation of the solvent afforded a crude mixture of compounds 15 and 16 (700 mg) as a brownish-orange semisolid. Compound 15 was purified by recrystallization from methanol. Compound 16 was purified from the resulting mother liquor by preparative TLC (eluent: $CH_2Cl_2$—MeOH—HOAc, 94:5:1).

Compound 15: MS m/e 276 (M+H).

Compound 16: $^1$H NMR (DMSO-$d_6$) δ8.64 (d, 1H), 8.08 (d, 1H), 7.92 (s, 1H), 7.82 (t, 1H), 7.70 (t, 1H), 7.38 (m, 5H), 3.30 (t, 2H), 3.16 (t, 2H); MS m/e 278 (M+H).

The synthesis of a representative example of an amine containing a terminal sulfonamide moiety is shown in General Method E.

General Method E

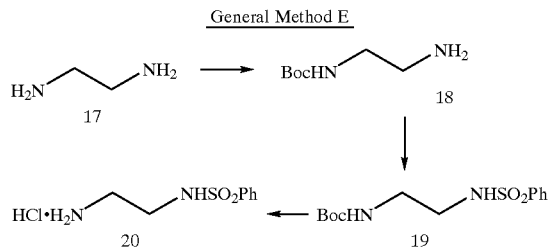

Preparation of Compound 18

To a solution of 1,2-ethylenediamine (compound 17, 10.80 g, 12.00 mL, 0.18 mol) in THF (30 mL) was added slowly BOC-ON (22.10 g, 0.09 mol) in THF (70 mL) over a period of 4 hours. The reaction mixture was stirred overnight, concentrated on a rotavapor, and the residue was dissolved in water (150 mL). The aqueous layer was acidified (pH ~5–6) with solid citric acid monohydrate, washed with ether (3×50 mL), and then treated (at 0° C.) with 6 N NaOH solution to pH ~12–13. The basic solution was extracted into ethyl acetate (3×100 mL), and the combined ethyl acetate layer was dried ($MgSO_4$) and concentrated to generate 7.23 g of monoprotected diamine, compound 18.

Compound 18: semisolid; $^1$H-NMR (CDCl$_3$) δ5.00 (broad, 1H), 3.20 (broad q, 2H), 2.80 (t, 2H), 1.45 (s, 9H), 1.25 (broad, 2H).

Preparation of Compound 19

A cooled (0–5° C.) solution of the compound 18 (0.321 g, 0.002 mol) in methylene chloride (5 mL) was treated sequentially with triethylamine (0.243 g, 0.33 mL, 0.0024 mol) and benzenesulfonyl chloride (0.423 g, 0.30 mL, 0.0024 mol). The ice-bath was removed and the mixture was stirred for an additional 0.5 hour, washed successively with water (2×5 mL), cold (0–5° C.) 0.5 N HCl (1×5 mL), 2% (NaHCO$_3$ solution (1×5 mL), and brine (1×5 mL). The solution was dried ($MgSO_4$), and the solvent was evaporated to give a residue which was washed several times with n-pentane to give 0.60 g of the sulfonamide derivative, compound 19.

Compound 19: white solid, mp 92–95° C.; $R_f$ (TLC, 5% methanol in methylene chloride) 0.55; $^1$H-NMR (CDCl$_3$) δ7.85 (d, 2H), 7.55 (m, 3H), 5.30 (broad d, 1H), 4.85 (broad, 1H), 3.25 (broad q, 2H), 3.10 (broad q, 2H), 1.40 (s, 9H).

Preparation of Compound 20

A solution of compound 19 (0.560 g, 0.0019 mol) in 1,4-dioxane (4 mL) was treated with 4 N HCl in dioxane (4 mL). The mixture was stirred at room temperature for 1 hour and concentrated at the rotavapor. The residue was washed several times with ethyl acetate and dried under vacuum to give 0.40 g of the amine salt, compound 20.

Compound 20: white solid, mp 178–180° C.; $^1$H-NMR (DMSO-$d_6$) δ8.20–8.00 (broad t, 4H), 7.80 (d, 2H), 7.60 (m, 3H), 2.95 (broad q, 2H), 2.80 (broad, 2H).

The synthesis of a representative alkoxyamine, containing a terminal sulfonamide moiety, is shown in General Method F.

General Method F

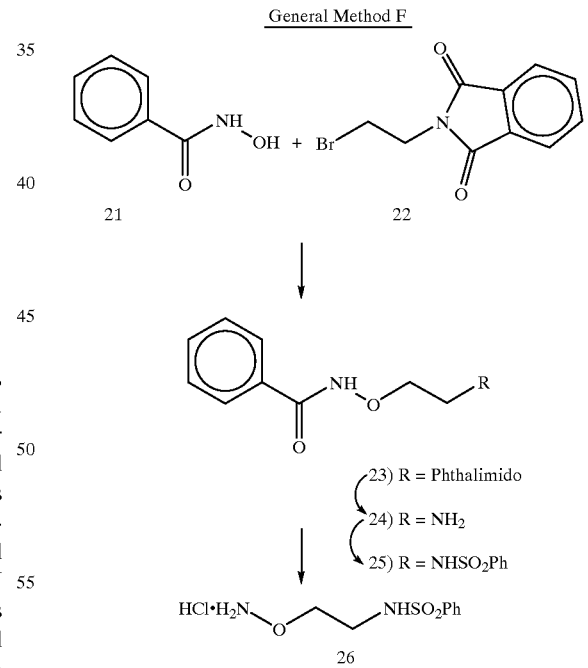

Preparation of Compound 23

To a solution of benzohydroxamic acid (compound 21, 5.00 g, 0.0365 mol) in DMF (50 mL) was slowly added sodium methoxide (2.50 g, 0.044 mol). The mixture was stirred for 10 minutes and to it was added N-(2-bromoethyl) phthalimide (compound 22, 9.00 g, 0.0333 mol). The reaction mixture was then stirred overnight, concentrated at the rotavapor, and partitioned between methylene chloride (200 mL) and 0.1 N NaOH (200 mL). The organic layer was separated, washed with water (2×30 mL), dried (MgSO$_4$) and concentrated to a small volume. Trituration with ethanol produced 4.30 g of compound 23 which was used without further purification; MS m/e 311 (M+H).

Preparation of Compound 24

A mixture of compound 23 (1.00 g, 0.0032 mol), hydrazine (1 mL) and 95% ethanol was held at reflux for 6 hours. After cooling, the reaction mixture was filtered and the filtrate was concentrated to give 0.575 g of compound 24 which was directly used in the next step; MS m/e 181 (M+H).

Preparation of Compound 25

Compound 25 was generated from compound 24 following the same procedure as described for the synthesis of Compound 19 (General Method E); the crude product was purified by flash column chromatography (eluant 20% ethyl acetate in methylene chloride) to give 0.75 g of compound 25; MS m/e 321 (M+H).

Preparation of Compound 26

A mixture of compound 25 (0.60 g, 1.87 mmol) and 6 N HCl (20 mL) was held at reflux for 3 hours, cooled to room temperature and filtered. The filtrate was concentrated in vacuo overnight, to generate the amine salt, compound 26; MS m/e 217 (M+H).

Preparation of Compound 27

2-Phenylquinazoline-4-carboxylic acid (compound 27) was prepared following a general procedure of Giardina et al, *J. Med. Chem.* 1997, 40, 1794–1807. This material can be incorporated into General Method A replacing compound 3.

27

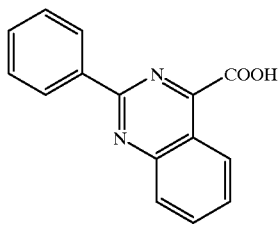

Preparation of the Compound of Example 11 by General Method A

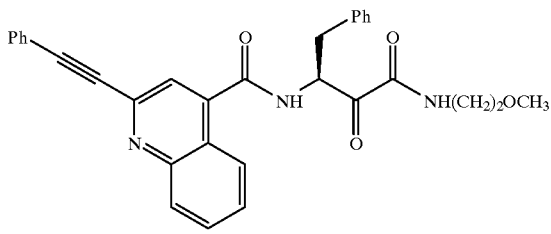

17: pale yellow solid; $^1$H-NMR (CDCl$_3$) δ8.10 (d, 1H), 7.95 (d, 1H), 7.75 (t, 1H), 7.70–7.10 (a series of m, 13H), 6.55 (d, 1H), 5.90 (m, 1H), 3.65–3.10 (a series of m, 6H), 3.40 (s, 3H), MS m/e 506 (M+H).

Preparation of the Compound of Example 96 by General Method B

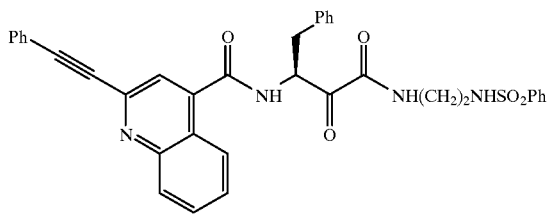

105: pale yellow solid; $^1$H-NMR (CDCl$_3$) δ8.10 (d, 1H), 7.95 (d, 1H), 7.80–7.10 (a series of m, 19H), 6.55 (d, 1H), 5.90 (m, 1H), 5.10 (t, 1H), 3.50 (m, 3H), 3.20 (m, 3H). MS m/e 631 (M+H).

Preparation of the Compound of Example 144 by General Method C

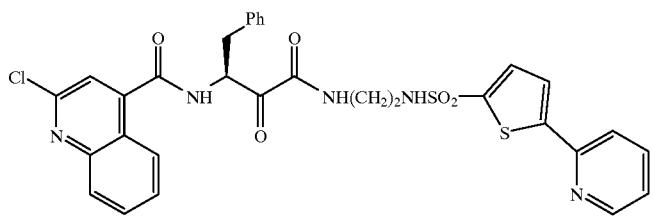

159: pale yellow solid; $^1$H-NMR (DMSO-d$_6$) δ9.35 (d, 1H), 8.90 (t, 1H), 8.50 (d, 1H), 8.10 (t, 1H), 8.00–7.70 (m, 7H), 7.55 (t, 2H), 7.40–7.10 (m, 6H), 5.50 (m, 1H), 3.30 (m, 2H), 3.00 (q, 3H), 2.75 (m, 1H). MS m/e 648 and 650 (M+H, with different isotopes of chlorine), 670 and 672 (M+Na, with different isotopes of chlorine).

EXAMPLE 159

Inhibition of Cysteine Protease Activity

To evaluate inhibitory activity, stock solutions (40 times concentrated) of each compound to be tested were prepared in 100% anhydrous DMSO and 5 μl of each inhibitor preparation was aliquoted into each of three wells of a 96-well plate. Recombinant human calpain I, prepared by the method of Meyer et al. (*Biochem. J.* 1996, 314: 511–519), was diluted into assay buffer (i.e., 50 mM Tris, 50 mM NaCl, 1 mM EDTA, 1 mM EGTA, and 5 mM β-mercaptoethanol, pH 7.5, including 0.2 mM Succ-Leu-Tyr-MNA), and 175 μl was aliquoted into the same wells containing the independent inhibitor stocks as well as to positive control wells containing 5 μl DMSO, but no compound. To start the reaction, 20 μl of 50 mM CaCl$_2$ in assay buffer was added to all wells of the plate, excepting three, which were used as background signal baseline controls. Substrate hydrolysis was monitored every 5 minutes for a total of 30 minutes. Substrate hydrolysis in the absence of inhibitor was linear for up to 15 minutes.

Inhibition of calpain I activity was calculated as the percent decrease in the rate of substrate hydrolysis in the presence of inhibitor relative to the rate in its absence. Comparison between the inhibited and control rates was made within the linear range for substrate hydrolysis. The IC$_{50}$S of inhibitors (concentration yielding 50% inhibition) were determined from the percent decrease in rates of substrate hydrolysis in the presence of five to seven different concentrations of the test compound. The results were plotted as percent inhibition versus log inhibitor concentration, and the IC$_{50}$ was calculated by fitting the data to the four-parameter logistic equation shown below using the program GraphPad Prism (GraphPad Software, Inc., San Diego, Calif.).

$$y = d + [(a-d)/(1+(x/c)^b)]$$

The parameters a, b, c, and d are defined as follows: a is % inhibition in the absence of inhibitor, b is the slope, c is the IC$_{50}$, and d is the % inhibition at an infinite concentration of inhibitor.

Results are presented Tables 2–5.

To demonstrate activity against another cysteine protease, cathepsin B (Calbiochem, cat#219364), assays were performed substantially the same as outlined above except that the cathepsin B was diluted into a different assay buffer consisting of 50 mM sodium acetate (pH 6.0)/1 mM EDTA/1 mM dithiothreitol and the substrate used was 0.1 mM Cbz-Phe-Arg-AMC (Bachem cat#I-1160). Additionally, the order of reagents added to the plate was altered because the enzyme is consitutively active. Following inhibitor addition to the plates, appropriate 2× concentrated stock dilutions of the enzyme preparations were made in assay buffer and 100 μl added to each well. The assay was initiated by addition of 100 μl of 2× concentrated stock dilution of substrate in assay buffer. Substrate hydrolysis was monitored using a Fluoriskan II (ex=390 nm; em=460 nm). Results are presented in Table 6.

EXAMPLE 160

Inhibition of Serine Protease Activity

To demonstrate activity against the serine protease α-chymotrypsin (Sigma Chem. Co. Cat. #C-3142) the protocol of Example 159 was followed except that the enzyme was diluted into assay buffer consisting of 50 mM Hepes (pH 7.5)/0.5M NaCl and the final substrate concentration used was 0.03 mM Succ-Ala-Ala-Pro-Phe-AMC (Bachem, Inc. Cat. #I-1465). Additionally, because α-chymotrypsin is not a calcium sensitive enzyme and is constitutively active, following addition of inhibitor stocks to the 96 well plates, 100 μl of a 2-fold concentrated stock of enzyme in dilution buffer was first added and the reaction was started by addition of 100 μl of a 2-fold concentrated stock of substrate in assay buffer. Substrate hydrolysis was monitored every 5 minutes up to 30 minutes using a Fluoroskan II (ex=390 nm em=460 nm). Results are listed in Table 6.

TABLE 2

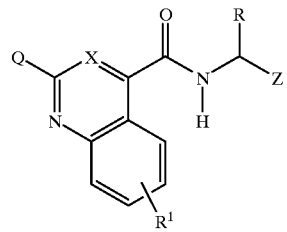

Q = Phenylethynyl
X = CH
R = CH$_2$C$_6$H$_5$
Z = COCONH—R$^7$

| Ex. | R$^7$ | Calpain I IC$_{50}$ nM** | Synth. Method | MAss Spectrum MH+ |
|---|---|---|---|---|
| 1 | CH$_2$C≡CH | (91%) | A | 486 |
| 2 | CH$_2$CF$_3$ | (98%) | A | 530 |
| 3 | CH$_2$CH═CH$_2$ | 210 | A | 488 |
| 4 | CH$_2$cyclopropane | (100%) | A | 502 |
| 5 | CH$_2$CH$_2$CN | (95%) | A | 501 |
| 6 | CH$_2$CH$_2$cyclohexene-1-yl | (89%) | A | 556 |
| 7 | CH$_2$CH(OCH$_3$)$_2$ | 110 | A | 536 |
| 8 | CH$_2$CH$_2$CH$_2$OCH$_2$CH$_2$OCH$_3$ | 570 | A | 564 |

TABLE 2-continued

Q = Phenylethynyl
X = CH
R = CH$_2$C$_6$H$_5$
Z = COCONH—R$^7$

| Ex. | R$^7$ | Calpain I IC$_{50}$ nM** | Synth. Method | MAss Spectrum MH+ |
|---|---|---|---|---|
| 9 | CH$_2$CH$_2$OCH$_2$CH$_2$OCH$_2$CH$_2$OC$_6$H$_{13}$ | 230 | A | 664 |
| 10 | CH$_2$CH$_2$OCH$_2$CH$_2$OH | 630 | A | 536 |
| 11 | CH$_2$CH$_2$OCH$_3$ | 480 | A | 506 |
| 12 | CH$_2$CH$_2$CH$_2$OH | (94%) | A | 506 |
| 13 | (CH$_2$)$_4$OH | (100%) | A | 520 |
| 14 | (CH$_2$)$_5$OH | (98%) | A | 534 |
| 15 | adamantyl | (41%) | A | 582 |
| 16 | cyclopropane | (100%) | A | 488 |
| 17 | (1-benzyl)piperidin-4-yl | 638 | A | 621 |
| 18 | (2-methylcyclohexyl) | (76%) | A | 544 |
| 19 | (4-methylcyclohexyl) | (91%) | A | 544 |
| 20 | (3-methylcyclohexyl) | (94%) | A | 544 |
| 21 | 4-piperidine-1-CO$_2$Et | (100%) | A | 603 |
| 22 | ε-caprolactam | 78 | A | 559 |
| 23 | CH(Bn)CH$_2$OH | (75%) | A | 582 |
| 24 | CH(CH$_2$OCH$_3$)CH(OH)Ph | (21%) | A | 582 |
| 25 | CH(CH$_2$OH)(CH$_2$)$_4$NHC(NHBoc)=NBoc | (42%) | A | 805 |
| 26 | CH(CH$_3$)-1-Naphthyl | (31%) | A | 602 |
| 27 | CH(CH$_3$)Ph | 510 | A | 552 |
| 28 | cyclohexan-2-ol | (61%) | A | 546 |
| 29 | [trans]cyclohexan-4-ol | 296 | A | 546 |
| 30 | cyclohexyl | (85%) | A | 530 |
| 31 | cyclopentane-1-CH$_2$OH | (27%) | A | 546 |
| 32 | tetrahydronaphth-1-yl | (31%) | A | 578 |
| 33 | piperon-5-yl | 388 | A | 582 |
| 34 | (CH$_2$)$_4$Ph | 227 | A | 580 |
| 35 | benzodioxan-6-yl | (71%) | A | 582 |
| 36 | CH$_2$Ph | 79* | B | 538 |
| 37 | CH$_2$(3,4-dimethoxy-Ph) | (95%) | A | 598 |
| 38 | CH$_2$(3,5-dimethoxy-Ph) | (92%) | A | 598 |
| 39 | CH$_2$(4-NH$_2$SO$_2$-Ph) | 184 | A | 617 |
| 40 | CH$_2$C$_6$H$_4$-3-NO$_2$ | (95%) | A | 583 |
| 41 | CH$_2$CH$_2$(3,4-dimethoxy-Ph) | (88%) | A | 612 |
| 42 | CH$_2$CH$_2$(4-NH$_2$SO$_2$-Ph) | 69 | A | 631 |
| 43 | CH$_2$CH$_2$Ph | 390 | A | 552 |
| 44 | CH$_2$CHPh$_2$ | (85%) | A | 628 |
| 45 | CH$_2$-pyrid-2-yl | 210 | A | 540 |
| 46 | CH$_2$-pyrid-3-yl | (91%) | A | 540 |
| 47 | CH$_2$-pyrid-4-yl | (98%) | A | 540 |
| 48 | CH$_2$CH$_2$-2-methyl-5-NO$_2$ imidazole | (95%) | A | 601 |
| 49 | CH$_2$CH$_2$-5-MeO-indole-3-yl | 160 | A | 621 |
| 50 | CH$_2$CH$_2$CH$_2$-imidazol-1-yl | (84%) | A | 556 |
| 51 | CH$_2$CH$_2$CH$_2$-morpholin-4-yl | 424 | A | 575 |
| 52 | CH$_2$CH$_2$CH$_2$-pyrrolidin-2-one | 366 | A | 573 |
| 53 | CH$_2$CH$_2$-Phthalimide | 226 | A | 621 |
| 54 | CH$_2$tetrahydrofuran-2-yl | (84%) | A | 532 |
| 55 | indan-2-yl | (60%) | A | 564 |
| 56 | CH$_2$CH$_2$NHCO(4-F-Ph) | 146 | A | 613 |
| 57 | CH$_2$CH$_2$NHCO(4-MeOPh) | (71%) | A | 625 |
| 58 | CH$_2$CH$_2$NHCO-2-furanyl | 98 | A | 585 |
| 59 | CH$_2$CH$_2$NHCO-morpholine | 248 | A | 604 |
| 60 | CH$_2$CH$_2$NHCOCH$_3$ | 140 | A | 533 |
| 61 | CH$_2$CH$_2$NHCONH(4-Br-Ph) | (94%) | A | 689 |
| 62 | CH$_2$CH$_2$NHCONH(4-MeOPh) | 190 | A | 640 |
| 63 | CH$_2$CH$_2$NHCONH-Adamant-1-yl | 257 | A | 668 |
| 64 | CH$_2$CH$_2$NHCONHPh | 67 | A | 610 |
| 65 | CH$_2$CH$_2$NHCOPh | (100%) | A | 595 |
| 66 | CH$_2$CH$_2$NHCSNH(4-MeOPh) | 113 | A | 656 |
| 67 | CH$_2$CH$_2$NHCSNH(4-NO$_2$Ph) | 93 | A | 671 |

TABLE 2-continued

Q = Phenylethynyl
X = CH
R = $CH_2C_6H_5$
Z = COCONH—$R^7$

| Ex. | $R^7$ | Calpain I $IC_{50}$ nM** | Synth. Method | MAss Spectrum MH+ |
|---|---|---|---|---|
| 68 | $CH_2CH_2NHSO_2$(2-$NO_2$-Ph) | 260 | A | 676 |
| 69 | $CH_2CH_2NHSO_2$(4-F-Ph) | 47 | A | 649 |
| 70 | $CH_2CH_2NHSO_2$-(1-methylimidazol-4-yl) | 137 | A | 635 |
| 71 | $CH_2CH_2NHSO_2$-(2,1,3-thiadiazol-4-yl) | 89 | A | 689 |
| 72 | $CH_2CH_2NHSO_2$-(2,5-dichloro-Ph) | (96%) | A | 699 |
| 73 | $CH_2CH_2NHSO_2$-(2-$MeO_2$C-thiophene-3-yl) | 220 | A | 695 |
| 74 | $CH_2CH_2NHSO_2$-(2-NC-Ph) | 132 | A | 656 |
| 75 | $CH_2CH_2NHSO_2$-(3,4-dichloro-Ph) | 100 | A | 699 |
| 76 | $CH_2CH_2NHSO_2$-(3,5-dimethylisoxazol-4-yl) | (98%) | A | 650 |
| 77 | $CH_2CH_2NHSO_2$-(3-NC-Ph) | 77 | A | 656 |
| 78 | $CH_2CH_2NHSO_2$-(3-$NO_2$-Ph) | (88%) | A | 676 |
| 79 | $CH_2CH_2NHSO_2$-(4-acetamido-Ph) | 43 | A | 688 |
| 80 | $CH_2CH_2NHSO_2$-(4-$CF_3$O-Ph) | 200 | A | 694 |
| 81 | $CH_2CH_2NHSO_2$-(4-MeO-Ph) | 62 | A | 661 |
| 82 | $CH_2CH_2NHSO_2$-(4-NC-Ph) | 70 | A | 656 |
| 83 | $CH_2CH_2NHSO_2$-(4-$NH_2$-Ph) | 70 | A | 646 |
| 84 | $CH_2CH_2NHSO_2$-(4-$NO_2$-Ph) | 26 | B | 676 |
| 85 | $CH_2CH_2NHSO_2$-(5-(BzNHCH$_2$)thiophen-2-yl) | 48 | A | 770 |
| 86 | $CH_2CH_2NHSO_2$-[5-(2-pyridinyl)thiophen-2-yl] | 31 | A | 712 |
| 87 | $CH_2CH_2NHSO_2$-(pyridin-3-yl) | 56* | C | 632 |
| 99 | $CH_2CH_2NHSO_2$-naphth-2-yl | 41 | A | 681 |
| 89 | $CH_2CH_2NHSO_2$-Quinolin-8-yl | 130 | A | 682 |
| 90 | $CH_2CH_2NHSO_2$-thiophene-2-yl | 76 | A | 637 |
| 91 | $CH_2CH_2NHSO_2CH$=CH—Ph | 42 | A | 657 |
| 92 | $CH_2CH_2NHSO_2CH_2$Ph | 94 | A | 645 |
| 93 | $CH_2CH_2NHSO_2CH_3$ | 180 | A | 569 |
| 94 | $CH_2CH_2NHSO_2NMe_2$ | 141 | A | 598 |
| 95 | $CH_2CH_2NHSO_2$Ph | 43 | A | 631 |
| 96 | $CH_2CH_2NHSO_2$Ph | 29* | B | 631 |
| 97 | $(CH_2)_3$NHBoc | (100%) | A | 605 |
| 98 | $(CH_2)_3$NHCONHPh | 126 | A | 624 |
| 99 | $(CH_2)_3NHSO_2$Me | 130 | A | 583 |
| 100 | $(CH_2)_3NHSO_2$Ph | 55 | A | 645 |
| 101 | $(CH_2)_6NHSO_2$(5-Cl-naphthalen-1-yl) | (84%) | A | 771 |
| 102 | $OCH_3$ | 82 | A | 538 |
| 103 | $OCH_2CH_3$ | 65 | A | 492 |
| 104 | OBn | 60 | A | 554 |
| 105 | $OCH_2CH_2NHSO_2$Ph | 128 | A | 647 |
| 106 | $(CH_2)_4CH(CO_2Me)$NHBoc | (97%) | A | 691 |
| 107 | $CH_2CH_2CO_2$tBu | (93%) | A | 576 |
| 108 | $CH_2CH_2$NH-L-Pro-$SO_2$Ph | (94%) | A | 728 |
| 109 | $CH(Bn)CO_2Me$ | 655 | A | 610 |
| 110 | $NMe_2$ | (43%) | A | 491 |
| 111 | $CH_2CH_2$O—COC(=$CH_2$)$CH_3$ | (95%) | A | 560 |

TABLE 3

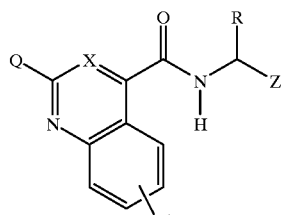

Q = phenylethynyl
X = CH
Z = COCONH—R$^7$

| Ex. | R$^7$ | R | Calpain I IC$_{50}$ nM** | Synth. Meth. | Mass Spect. MH+ |
|---|---|---|---|---|---|
| 112 | CH$_2$CH$_2$OCH$_3$ | iBu | (95%) | B | 472 |
| 113 | CH$_2$CH(OCH$_3$)$_2$ | iBu | (92%) | A | 502 |
| 114 | CH$_2$CH$_2$OCH$_2$CH$_2$OH | iBu | (93%) | A | 502 |
| 115 | CH$_2$CH$_2$NHCO$_2$CH$_2$Ph | iBu | (100%) | B | 591 |
| 116 | CH$_2$CH$_2$NHCONHPh | iBu | (89%) | A | 576 |
| 117 | CH$_2$CH$_2$NHSO$_2$Ph | iBu | (82%) | A | 597 |
| 118 | CH$_2$CH$_2$NHSO$_2$(3,4-Cl$_2$Ph) | iBu | 120 | B | 666 |
| 119 | (CH$_2$)$_3$NHSO$_2$Ph | iBu | (80%) | A | 611 |
| 120 | CH$_2$CH$_2$OCH$_3$ | Et | (92%) | A | 444 |
| 121 | CH$_2$CH(OCH$_3$)$_2$ | Et | (94%) | A | 474 |
| 122 | CH$_2$CH$_2$NHSO$_2$Ph | Et | (89%) | A | 569 |
| 123 | CH$_2$CH$_2$NHSO$_2$(3,4-Cl$_2$Ph) | Et | 58 | A | 637 |
| 124 | (CH$_2$)$_3$NHSO$_2$Ph | Et | 80 | A | 583 |
| 125 | CH$_2$CH$_2$NHCONHPh | Et | (32%) | A | 548 |
| 126 | CH$_2$CH$_2$NHSO$_2$(3,4-Cl$_2$Ph) | Bu | 39 | A | 665 |
| 127 | CH$_2$CH$_2$NHSO$_2$(4-NO$_2$Ph) | Bu | 29 | A | 642 |
| 128 | CH$_2$CH$_2$NHSO$_2$(3,4-Cl$_2$Ph) | Pr | 187 | A | 651 |
| 129 | CH$_2$CH$_2$NHSO$_2$(4-NO$_2$Ph) | Pr | 27 | A | 628 |

TABLE 4

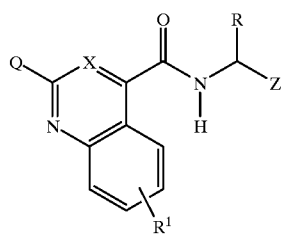

X = CH
R = CH$_2$C$_6$H$_5$
Z = COCONH—R$^7$

| Ex. | Q | R$^7$ | Calpain I IC$_{50}$ nM** | Synth Meth. | Mass Spec. MH+ |
|---|---|---|---|---|---|
| 130 | PhCH=CH | Bu | 105 | D | 506 |
| 131 | H | CH$_2$CH$_2$NHSO$_2$Ph | (97%)* | C | 531 |
| 132 | H(N-oxide) | CH$_2$CH$_2$NHSO$_2$Ph | (96%) | D | 547 |
| 133 | HO | CH$_2$CH$_2$NHSO$_2$Ph | (95%) | D | 547 |
| 134 | CH$_3$O | CH$_2$CH$_2$NHSO$_2$Ph | (17%) | D | 434 |
| 135 | Piperidin-1-yl | CH$_2$CH$_2$NHSO$_2$Ph | (91%) | D | 624 |

TABLE 4-continued

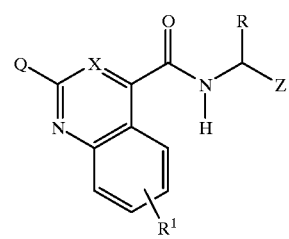

X = CH
R = CH$_2$C$_6$H$_5$
Z = COCONH—R$^7$

| Ex. | Q | R$^7$ | Calpain I IC$_{50}$ nM** | Synth Meth. | Mass Spec. MH+ |
|---|---|---|---|---|---|
| 136 | Pyridin-3-yl | CH$_2$CH$_2$NHSO$_2$Ph | (99%) | D | 608 |
| 137 | PhCH$_2$CH$_2$ | CH$_2$CH$_2$NHSO$_2$Ph | 116 | D | 635 |
| 138 | Cl | CH$_2$CH$_2$NHSO$_2$Ph | 28* | C | 565 |
| 139 | Cl | CH$_2$CH(CH$_3$)NHSO$_2$Ph [S] | 59 | C | 579 |
| 140 | Cl | CH$_2$CH(CH$_3$)NHSO$_2$Ph [R] | 155 | C | 579 |
| 141 | Cl | CH$_2$CH$_2$NHSO$_2$(Pyridin-3-yl) | 87* | C | 566 |
| 142 | CH$_3$ | CH$_2$CH$_2$NHSO$_2$[5-(2-pyridinyl)thiophen-2-yl] | 24* | C | 628 |
| 143 | 2-CH$_3$*** | CH$_2$CH$_2$NHSO$_2$[5-(2-pyridinyl)thiophen-2-yl] | 35* | C | 658 |
| 144 | Cl | CH$_2$CH$_2$NHSO$_2$[5-(2-pyridinyl)thiophen-2-yl] | 14 | C | 648 |
| 145 | Cyclopropyl | CH$_2$CH$_2$NHSO$_2$[5-(2-pyridinyl)thiophen-2-yl] | 71 | C | 654 |
| 146 | Thiophen-2-yl | CH$_2$CH$_2$NHSO$_2$[5-(2-pyridinyl)thiophen-2-yl] | 85 | C | 696 |
| 147 | Cl | CH$_2$CH$_2$SO$_2$NHPh | 81 | C | 565 |
| 148 | Cl | CH$_2$CH$_2$SO$_2$NH(4-F-Ph) | 75 | C | 583 |

Footnotes to Tables 2–4:

*single enantiomer

**(% inhibition of calpain I at 10,000 nM)

***R$^1$ is 6-methoxy

TABLE 5

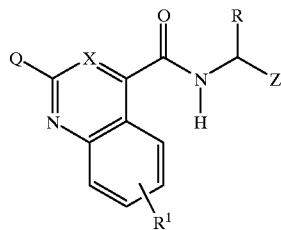

Z = COCONHR[7]

| Ex | Q | X | R | R[7] | Calpain I IC$_{50}$** | Synth Meth. | Mass Spec MH+ |
|---|---|---|---|---|---|---|---|
| 149 | Cl | CH | n-Bu | CH$_2$CH$_2$NHSO$_2$(4-NO$_2$Ph) | 23 | B | 576 |
| 150 | Cl | CH | n-Pr | CH$_2$CH$_2$NHSO$_2$(4-NO$_2$Ph) | (78%) | B | 562 |
| 151 | Cl | CH | n-Bu | CH$_2$CH$_2$NHSO$_2$(3,4-Cl$_2$Ph) | 217 | B | 599 |
| 152 | Cl | CH | n-Pr | CH$_2$CH$_2$NHSO$_2$(3,4-Cl$_2$Ph) | 325 | B | 585 |
| 153 | Ph | N | Bn | CH$_2$CH$_2$NHSO$_2$Ph | (95%) | C | 608 |
| 154 | Ph | N | Bn | CH$_2$CH$_2$NHSO$_2$[5-(2-pyridinyl)thiophen-2-yl] | 83 | C | 691 |
| 155 | Cl | CH | n-Bu | CH$_2$CH$_2$NHSO$_2$[5-(2-pyridinyl)thiophen-2-yl] | 31 | B | 614 |
| 156 | Cl | CH | n-Pr | CH$_2$CH$_2$NHSO$_2$[5-(2-pyridinyl)thiophen-2-yl] | 43 | B | 600 |
| 157 | Cl | CH | CH$_3$O—CH$_2$ | CH$_2$CH$_2$NHSO$_2$[5-(2-pyridinyl)thio-phen-2-yl | 61 | B | 603 |
| 158 | Cl | CH | CH$_3$O—CH$_2$ | CH$_2$CH$_2$NHSO$_2$Ph | (94%) | B | 519 |

TABLE 6

Inhibition of Cathepsin B and α-Chymotrypsin

| Cmpd. of Ex. | Cath. B IC$_{50}$ (nM) | Chymotrypsin IC$_{50}$ (nM) |
|---|---|---|
| 100 | 360 | 36 |
| 96 | 375 | 66 |
| 103 | 435 | 380 |
| 104 | 330 | 1160 |
| 84 | 348 | 14 |
| 86 | 1030 | 475 |

It is intended that each of the patents, applications, and printed publications mentioned in this patent document be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A compound having the Formula I:

wherein:
X is CH, or CQ$^1$, with the proviso that when X is CQ$^1$, at least one of Q or Q$^1$ is H;

R is selected from the group consisting of H, alkyl having from one to 6 carbons, arylalkyl having from 7 to 15 carbons, heteroalkyl in which the ring contains from 5 to 14 ring atoms, heteroarylalkyl in which the heteroaryl ring contains from 5 to 14 ring atoms, alkoxyalkyl, a side chain of a naturally occurring amino acid in the R or S configuration, and (CH$_2$)$_n$NH-L, said alkyl, arylalkyl, heteroalkyl, and heteroarylalkyl groups being optionally substituted with one or more J groups;

L is selected from the group consisting of alkoxycarbonyl having from 2 to 7 carbons, arylalkoxycarbonyl in which the arylalkoxy group contains 7 to 15 carbons, S(=O)$_2$R$^2$, and N-nitroimino;

R² is selected from the group consisting of lower alkyl, and aryl having from 6 to 14 carbons;

R¹ is selected from the group consisting of H, halogen, cyano, nitro, —S(=O)₂—OH, hydroxyl, alkyl, alkoxy, hydroxymethyl, alkoxymethyl, arylalkyl, carboxyl, alkoxycarbonyl, alkylcarbonyloxy, haloalkyl, N(RR³), and acyl;

R³ is the same as R;

Q is selected from the group consisting of H, lower alkyl, cycloalkyl, hydroxyl, alkoxy, halogen, arylalkyl having from 7 to 15 carbons, arylalkeny having from 8 to 16 carbons, arylalkynyl having from 8 to 16 carbons, aryl having from 6 to 14 carbons, heteroaryl having from 5 to 14 ring atoms, heteroalkyl having from 5 to 14 ring atoms, cycloalkyl having from 3 to 10 carbons, S—R, S(=O)R, S(=O)₂R, N(RR³), and NHS(=O)₂R, said arylalkyl, arylalkenyl, arylalkynyl, aryl, heteroaryl, and heteroalkyl groups being optionally substituted with one or more J groups;

Q¹ is the same as Q;

Z is COCONH-R⁷;

R⁷ is selected from the group consisting of K, —A—N(R⁸)—G, —O—A—N(R⁸)—G, —A—SO₂N(R⁸)(R⁹), and —O—A—SO₂N(R⁸) (R⁹);

K is selected from the gorup consisting of alkyl, aleknyl, alkynyl, cycloalkyl, heteroalkyl, heteroaryl, aryl, arylalkyl, heterocycloalkyl, alkoxy, alkoxyalkyl, arylalkyloxy, and N(RR³), said K groups being optionally substituted with one or more J groups;

A is lower alkylene optionally substituted with one or more J groups;

R⁸ is selected from the group consisting of H and lower alkyl;

R⁹ is selected from the group consisting of H, alkyl, aryl, and heterocyclyl, said alkyl, aryl, and heterocyclyl groups being optionally substituted with one or more J groups;

G is selected from the group consisting of C(=O)aryl, C(=O)heteroaryl, C(=O)heteroalkyl, alkanoyl, C(=S)NH(aryl), C(=O)NH(aryl), C(=O)NH(cycloalkyl), CO₂-(aryl), C(=O)alkyl, CO₂(alkyl), CO₂(arylalkyl), alkylsulfonyl, alkenylsulfonyl, arylsulfonyl, heteroarylsulfonyl, a side chain of a naturally occurring amino acid in the R or S configuration, a blocking group, and SO₂N(RR³), said G groups being optionally substituted with one or more J groups;

J is selected from the group consisting of H, halogen, cyano, nitro, hydroxyl, alkyl, alkoxy, aryl, arylalkyl, alkoxycarbonyl, alkylcarbonyloxy, alkenylcarbonyloxy, haloalkyl, aminoalkyl, haloalkoxy, SO₂N(RR³), SO₂NH(aryl), SO₂NH(heteroaryl), NHC(=O)NH(aryl), NH(C=O)NH(heteroaryl), NHSO₂(aryl), NHC(=O)alkyl, NHC(=O)aryl, NHC(=O)heteroaryl, N(RR³), and NH=C(NH₂)₂;

n is an integer from 2 to 6;

or a pharmaceutically acceptable salt thereof;
with the proviso that when R⁷ is K, then Q is selected from the group consisting of optionally substituted arylalkenyl and optionally substituted arylalkynyl; and
with the further proviso that when K is alkyl, then X is not CH when Q is optionally substituted arylalkynyl.

2. The compound of claim 1 wherein X is CH.

3. The compound of claim 1 wherein R is selected from the group consisting of alkyl having from 2 to 4 carbons, and arylalkyl.

4. The compound of claim 3 wherein R is benzyl.

5. The compound of claim 1 wherein R¹ is H or alkoxy.

6. The compound of claim 5 wherein R¹ is H.

7. The compound of claim 1 wherein Q is selected from the group consisting of arylalkynyl, aryl and halo.

8. The compound of claim 7 wherein Q is phenylalkynyl.

9. The compound of claim 1 wherein A is selected from the group consisting of (CH₂)ₙ wherein n is 2 or 3, and (CH₂)ᵥCH₂-J where v is an integer from 1 to 6.

10. The compound of claim 9 wherein A is (CH₂)ᵥCH₂-J, where v is 2 or 3.

11. The compound of claim 1 wherein K is selected from the group consisting of alkyl, hydroxyalkyl, haloalkyl, alkynyl, heterocycloalkyl, arylalkyl, and heteroalkyl.

12. The compound of claim 1 wherein G is selected from the gorup consisting of substituted or unsubstituted C(=O) aryl, C(=O)heteroaryl, arylsulfonyl, and heteroarylsulfonyl.

13. The compound of claim 12 wherein G is selected from the group consisting of unsubstituted arylsulfonyl, substituted arylsulfonyl, unsubstituted heteroarylsulfonyl and substituted heteroarylsulfonyl.

14. The compound of claim 1 wherein X is CH, Z is COCONH-K, R₁ is H, and R is selected from the group consisting of alkyl having from 2 to 4 carbons and arylalkyl.

15. The compound of claim 14 wherein R is benzyl.

16. The compound of claim 1 wherein X is CH, Z is COCONH-K, R₁ is H, R is selected from the group consisting of alkyl having from 2 to 4 carbons and arylalkyl, and Q is arylalkynyl.

17. The compound of claim 16 wherein R is benzyl.

18. The compound of claim 16 wherein Q is phenylethynyl.

19. A compound as described in Tables 2–5 below:

TABLE 2

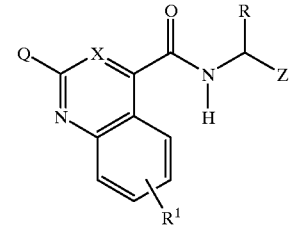

Q = Phenylethynyl
X = CH
R = CH₂C₆H₅
Z = COCONH—R⁷
R¹ = H

| Ex | R⁷ |
|---|---|
| 1 | CH₂C≡CH |
| 2 | CH₂CF₃ |
| 3 | CH₂CH=CH₂ |
| 4 | CH₂cyclopropane |
| 5 | CH₂CH₂CN |
| 6 | CH₂CH₂cyclohexene-1-yl |
| 7 | CH₂CH(OCH₃)₂ |
| 8 | CH₂CH₂CH₂OCH₂CH₂OCH₃ |
| 9 | CH₂CH₂OCH₂CH₂OCH₂CH₂OC₆H₁₃ |
| 10 | CH₂CH₂OCH₂CH₂OH |
| 11 | CH₂CH₂OCH₃ |
| 12 | CH₂CH₂CH₂OH |
| 13 | (CH₂)₄OH |
| 14 | (CH₂)₅OH |
| 15 | adamantyl |
| 16 | cyclopropane |
| 17 | (1-benzyl)piperidin-4-yl |
| 18 | (2-methylcyclohexyl) |

TABLE 2-continued

Q = Phenylethynyl
X = CH
R = CH$_2$C$_6$H$_5$
Z = COCONH—R$^7$
R$^1$ = H

| Ex | R$^7$ |
|---|---|
| 19 | (4-methylcyclohexyl) |
| 20 | (3-methylcyclohexyl) |
| 21 | 4-piperidine-1-CO$_2$Et |
| 22 | ε-caprolactam |
| 23 | CH(Bn)CH$_2$OH |
| 24 | CH(CH$_2$OCH$_3$)CH(OH)Ph |
| 25 | CH(CH$_2$OH)(CH$_2$)$_4$NHC(NHBoc)=NBoc |
| 26 | CH(CH$_3$)-1-Naphthyl |
| 27 | CH(CH$_3$)Ph |
| 28 | cyclohexan-2-ol |
| 29 | [trans]cyclohexan-4-ol |
| 30 | cyclohexyl |
| 31 | cyclopentane-1-CH$_2$OH |
| 32 | tetrahydronaphth-1-yl |
| 33 | piperon-5-yl |
| 34 | (CH$_2$)$_4$Ph |
| 35 | benzodioxan-6-yl |
| 36 | CH$_2$Ph |
| 37 | CH$_2$(3,4-dimethoxy-Ph) |
| 38 | CH$_2$(3,5-dimethoxy-Ph) |
| 39 | CH$_2$(4-NH$_2$SO$_2$-Ph) |
| 40 | CH$_2$-C$_6$H$_4$-3-NO$_2$ |
| 41 | CH$_2$CH$_2$(3,4-dimethoxy-Ph) |
| 42 | CH$_2$CH$_2$(4-NH$_2$SO$_2$-Ph) |
| 43 | CH$_2$CH$_2$Ph |
| 44 | CH$_2$CHPh$_2$ |
| 45 | CH$_2$-pyrid-2-yl |
| 46 | CH$_2$-pyrid-3-yl |
| 47 | CH$_2$-pyrid-4-yl |
| 48 | CH$_2$CH$_2$-2-methyl-5-NO$_2$-imidazole |
| 49 | CH$_2$CH$_2$-5-MeO-indole-3-yl |
| 50 | CH$_2$CH$_2$CH$_2$-imidazol-1-yl |
| 51 | CH$_2$CH$_2$CH$_2$-morpholin-4-yl |
| 52 | CH$_2$CH$_2$CH$_2$-pyrrolidin-2-one |
| 53 | CH$_2$CH$_2$-Phthalimide |
| 54 | CH$_2$tetrahydrofuran-2-yl |
| 55 | indan-2-yl |
| 56 | CH$_2$CH$_2$NHCO(4-F-Ph) |
| 57 | CH$_2$CH$_2$NHCO (4-MeOPh) |
| 58 | CH$_2$CH$_2$NHCO-2-furanyl |
| 59 | CH$_2$CH$_2$NHCO-morpholine |
| 60 | CH$_2$CH$_2$NHCOCH$_3$ |
| 61 | CH$_2$CH$_2$NHCONH(4-Br-Ph) |
| 62 | CH$_2$CH$_2$NHCONH(4-MeOPh) |
| 63 | CH$_2$CH$_2$NHCONH-Adamant-1-yl |
| 64 | CH$_2$CH$_2$NHCONHPh |
| 65 | CH$_2$CH$_2$NHCOPh |
| 66 | CH$_2$CH$_2$NHCSNH(4-MeOPh) |
| 67 | CH$_2$CH$_2$NHCSNH(4-NO$_2$Ph) |
| 68 | CH$_2$CH$_2$NHSO$_2$(2-NO$_2$-Ph) |
| 69 | CH$_2$CH$_2$NHSO$_2$(4-F-Ph) |
| 70 | CH$_2$CH$_2$NHSO$_2$-(1-methylimidazol-4-yl) |
| 71 | CH$_2$CH$_2$NHSO$_2$-(2,1,3-thiadiazol-4-yl) |
| 72 | CH$_2$CH$_2$NHSO$_2$- (2,5-dichloroph) |
| 73 | CH$_2$CH$_2$NHSO$_2$-(2-MeO$_2$C-thiophene-3-yl) |
| 74 | CH$_2$CH$_2$NHSO$_2$-(2-NC-Ph) |
| 75 | CH$_2$CH$_2$NHSO$_2$-(3,4-dichloro-Ph) |
| 76 | CH$_2$CH$_2$NHSO$_2$-(3,5-dimethylisoxazol-4-yl) |
| 77 | CH$_2$CH$_2$NHSO$_2$-(3-NC-Ph) |
| 78 | CH$_2$CH$_2$NHSO$_2$-(3-NO$_2$-Ph) |

TABLE 2-continued

Q = Phenylethynyl
X = CH
R = CH$_2$C$_6$H$_5$
Z = COCONH—R$^7$
R$^1$ = H

| Ex | R$^7$ |
|---|---|
| 79 | CH$_2$CH$_2$NHSO$_2$-(4-acetamido-Ph) |
| 80 | CH$_2$CH$_2$NHSO$_2$-(4-CF$_3$O-Ph) |
| 81 | CH$_2$CH$_2$NHSO$_2$-(4-MeO-Ph) |
| 82 | CH$_2$CH$_2$NHSO$_2$-(4-NC-Ph) |
| 83 | CH$_2$CH$_2$NHSO$_2$-(4-NH$_2$-Ph) |
| 84 | CH$_2$CH$_2$NHSO$_2$-(4-NO$_2$-Ph) |
| 85 | CH$_2$CH$_2$NHSO$_2$-(5-(BzNHCH$_2$)thiophen-2-yl) |
| 86 | CH$_2$CH$_2$NHSO$_2$-[5-(2-pyridinyl)thiophen-2-yl] |
| 87 | CH$_2$CH$_2$NHSO$_2$-(pyridin-3-yl) |
| 88 | CH$_2$CH$_2$NHSO$_2$-naphth-2-yl |
| 89 | CH$_2$CH$_2$NHSO$_2$-Quinolin-8-yl |
| 90 | CH$_2$CH$_2$NHSO$_2$-thiophene-2-yl |
| 91 | CH$_2$CH$_2$NHSO$_2$CH=CH-Ph |
| 92 | CH$_2$CH$_2$NHSO$_2$CH$_2$Ph |
| 93 | CH$_2$CH$_2$NHSO$_2$CH$_3$ |
| 94 | CH$_2$CH$_2$NHSO$_2$NMe$_2$ |
| 95 | CH$_2$CH$_2$NHSO$_2$Ph |
| 96 | CH$_2$CH$_2$NHSO$_2$Ph |
| 97 | (CH$_2$)$_3$NHBoc |
| 98 | (CH$_2$)$_3$NHCONHPh |
| 99 | (CH$_2$)$_3$NHSO$_2$Me |
| 100 | (CH$_2$)$_3$NHSO$_2$Ph |
| 101 | (CH$_2$)$_6$NHSO$_2$(5-Cl-naphthalen-1-yl) |
| 102 | OCH$_3$ |
| 103 | OCH$_2$CH$_3$ |
| 104 | OBn |
| 105 | OCH$_2$CH$_2$NHSO$_2$Ph |
| 106 | (CH$_2$)$_4$CH(CO$_2$Me)NHBoc |
| 107 | CH$_2$CH$_2$CO$_2$tBu |
| 108 | CH$_2$CH$_2$NH-L-Pro-SO$_2$Ph |
| 109 | CH(Bn)CO$_2$Me |
| 110 | NMe$_2$ |
| 111 | CH$_2$CH$_2$O—COC(=CH$_2$)CH$_3$ |

TABLE 3

Q = phenylethynyl
X = CH
Z = COCONH—R$^7$
R$^1$ = H

| Ex. | R$^7$ | R |
|---|---|---|
| 112 | CH$_2$CH$_2$OCH$_3$ | iBu |
| 113 | CH$_2$CH(OCH$_3$)$_2$ | iBu |
| 114 | CH$_2$CH$_2$OCH$_2$CH$_2$OH | iBu |
| 115 | CH$_2$CH$_2$NHCO$_2$CH$_2$Ph | iBu |
| 116 | CH$_2$CH$_2$NHCONHPh | iBu |

TABLE 3-continued

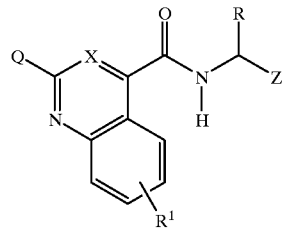

Q = phenylethynyl
X = CH
Z = COCONH—$R^7$
$R^1$ = H

| Ex. | $R^7$ | R |
|---|---|---|
| 117 | $CH_2CH_2NHSO_2Ph$ | iBu |
| 118 | $CH_2CH_2NHSO_2(3,4-Cl_2Ph)$ | iBu |
| 119 | $(CH_2)_3NHSO_2Ph$ | iBu |
| 120 | $CH_2CH_2OCH_3$ | Et |
| 121 | $CH_2CH(OCH_3)_2$ | Et |
| 122 | $CH_2CH_2NHSO_2Ph$ | Et |
| 123 | $CH_2CH_2NHSO_2(3,4-Cl_2Ph)$ | Et |
| 124 | $(CH_2)_3NHSO_2Ph$ | Et |
| 125 | $CH_2CH_2NHCONHPh$ | Et |
| 126 | $CH_2CH_2NHSO_2(3,4-Cl_2Ph)$ | Bu |
| 127 | $CH_2CH_2NHSO_2(4-NO_2Ph)$ | Bu |
| 128 | $CH_2CH_2NHSO_2(3,4-Cl_2Ph)$ | Pr |
| 129 | $CH_2CH_2NHSO_2(4-NO_2Ph)$ | Pr |

TABLE 4

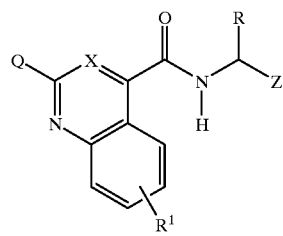

X = CH
R = $CH_2C_6H_5$
Z = COCONH—$R^7$
$R^1$ = H

| Ex. | Q | $R^7$ |
|---|---|---|
| 130 | PhCH=CH | Bu |
| 131 | H | $CH_2CH_2NHSO_2Ph$ |
| 132 | H(N-oxide) | $CH_2CH_2NHSO_2Ph$ |
| 133 | HO | $CH_2CH_2NHSO_2Ph$ |
| 134 | $CH_3O$ | $CH_2CH_2NHSO_2Ph$ |
| 135 | Piperidin-1-yl | $CH_2CH_2NHSO_2Ph$ |
| 136 | Pyridin-3-yl | $CH_2CH_2NHSO_2Ph$ |
| 137 | $PhCH_2CH_2$ | $CH_2CH_2NHSO_2Ph$ |
| 138 | Cl | $CH_2CH_2NHSO_2Ph$ |
| 139 | Cl | $CH_2CH(CH_3)NHSO_2Ph$ [S] |
| 140 | Cl | $CH_2CH(CH_3)NHSO_2Ph$ [R] |
| 141 | Cl | $CH_2CH_2NHSO_2(Pyridin-3-yl)$ |
| 142 | $CH_3$ | $CH_2CH_2NHSO_2$[5-(2-pyridinyl) thiophen-2-yl] |
| 143 | 2-$CH_3$*** | $CH_2CH_2NHSO_2$[5-(2-pyridinyl) thiophen-2-yl] |
| 144 | Cl | $CH_2CH_2NHSO_2$[5-(2-pyridinyl) thiophen-2-yl] |

TABLE 4-continued

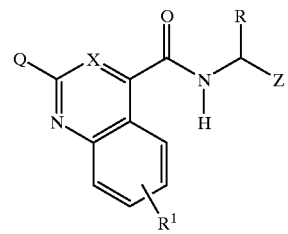

X = CH
R = $CH_2C_6H_5$
Z = COCONH—$R^7$
$R^1$ = H

| Ex. | Q | $R^7$ |
|---|---|---|
| 145 | Cyclo-propyl | $CH_2CH_2NHSO_2$[5-(2-pyridinyl) thiophen-2-yl] |
| 146 | Thiophen-2-yl | $CH_2CH_2NHSO_2$[5-(2-pyridinyl) thiophen-2-yl] |
| 147 | Cl | $CH_2CH_2SO_2NHPh$ |
| 148 | Cl | $CH_2CH_2SO_2NH(4-F-Ph)$ |

***denotes that $R^1$ is 6-methoxy

TABLE 5

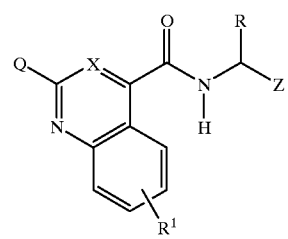

Z = COCONH$R^7$
$R^1$ = H

| Ex | Q | X | R | $R^7$ |
|---|---|---|---|---|
| 149 | Cl | CH | n-Bu | $CH_2CH_2NHSO_2(4-NO_2Ph)$ |
| 150 | Cl | CH | n-Pr | $CH_2CH_2NHSO_2(4-NO_2Ph)$ |
| 151 | Cl | CH | n-Bu | $CH_2CH_2NHSO_2(3,4-Cl_2Ph)$ |
| 152 | Cl | CH | n-Pr | $CH_2CH_2NHSO_2(3,4-Cl_2Ph)$ |
| 155 | Cl | CH | n-Bu | $CH_2CH_2NHSO_2$[5-(2-pyridinyl) thiophen-2-yl] |
| 156 | Cl | CH | n-Pr | $CH_2CH_2NHSO_2$[5-(2-pyridinyl) thiophen-2-yl] |
| 157 | Cl | CH | $CH_3O-CH_2$ | $CH_2CH_2NHSO_2$[5-(2-pyridinyl) thio-phen-2-yl |
| 158 | Cl | CH | $CH_3O-CH_2$ | $CH_2CH_2NHSO_2Ph$ |

20. A composition for inhibiting a serine protease or a cysteine protease comprising a compound of claim 1 and a pharmaceutically acceptable carrier.

21. A method for inhibiting a serine protease or a cysteine protease comprising contacting a protease selected from the group consisting of serine proteases and cysteine proteases with an inhibitory amount of a compound of claim 1.

* * * * *

UNITED STATES PATENT AND TRADEMARK OFFICE
CERTIFICATE OF CORRECTION

PATENT NO. : 6,083,944
DATED : July 4, 2000
INVENTOR(S) : Chatterjee et al.

It is certified that error appears in the above-identified patent and that said Letters Patent is hereby corrected as shown below:

Title page,
Item [56], References Cited, OTHER PUBLICATIONS,
In "Harbeson, S.L. et al.," please delete "β-Keto" and insert therefor -- α-Keto --;

Column 4,
Line 5, please delete "C(=)aryl" and insert therefor -- C(=O)aryl -- and please delete "C(=)heteroaryl" and insert therefor -- C(=O)heteroaryl --;

Column 6,
Line 27, please delete "reacements" and insert therefor -- racemates --;

Column 8,
Table 1, Column 2, 14$^{th}$ line of text, please delete "H$_2$N- CH$_2$- CH$_2$CH$_2$-" and insert therefor -- H$_2$N-CH$_2$-CH$_2$-CH$_2$- --;

Column 9,
Line 38, please delete "piperdine" and insert therefor --piperidine --;

Column 11,
Line 61, please delete "(3x250 mL)" and insert therefor -- (1x250 mL) --;

Column 20,
Line 7, please insert -- in -- between "presented" and "Tables";
Line 9, please delete "asays" and insert therefor -- assays --;
Line 15, please delete "consitutively" and insert therefor -- constitutively --;
Table 2, Column 5, please delete "MAss" and insert therefor -- Mass --;

Column 21,
Table 2, line 40, please delete "CH$_2$C$_6$H$_4$-3-NO$_2$" and insert therefor -- CH$_2$-C$_6$H$_4$-3-NO$_2$ --;

UNITED STATES PATENT AND TRADEMARK OFFICE
CERTIFICATE OF CORRECTION

PATENT NO. : 6,083,944
DATED : July 4, 2000
INVENTOR(S) : Chatterjee et al.

It is certified that error appears in the above-identified patent and that said Letters Patent is hereby corrected as shown below:

Column 27,
Table 5, line 150, please delete "$CH_2CH_2NHSO_{2(4}NO_2Ph$" and insert therefor -- $CH_2CH_2NHSO_2(4-NO_2Ph)$ --;
Table 5, after last line, please insert -- **(% inhibition of calpain I at 10,000 nM) --;

Column 29,
Line 11, please delete "arylalkeny" and insert therefor -- arylalkenyl --;
Line 24, please delete "gorup" and insert therefor -- group --;
Line 25, please delete "aleknyl" and insert therefor -- alkenyl --;

Column 30, claim 12,
Line 16, please delete "gorup" and insert therefor -- group --.

Signed and Sealed this

Fifth Day of March, 2002

*Attest:*

*Attesting Officer*

JAMES E. ROGAN
*Director of the United States Patent and Trademark Office*